United States Patent
Reinauer et al.

(10) Patent No.: US 11,318,229 B2
(45) Date of Patent: May 3, 2022

(54) METHOD FOR PRODUCING AN IMPLANT USING A CALCIUM CARBONATE-CONTAINING COMPOSITE POWDER COMPRISING MICROSTRUCTURED PARTICLES

(71) Applicant: Karl Leibinger Medizintechnik GmbH & Co. KG, Mühlheim (DE)

(72) Inventors: Frank Reinauer, Mühlheim (DE); Siegmund Luger, Mühlheim (DE); Marijan Vucak, Mühlheim (DE)

(73) Assignee: Karl Leibinger Medizintechnik GmbH & Co. KG, Mühlheim (DE)

( * ) Notice: Subject to any disclaimer, the term of this patent is extended or adjusted under 35 U.S.C. 154(b) by 560 days.

(21) Appl. No.: 16/331,575

(22) PCT Filed: Aug. 17, 2017

(86) PCT No.: PCT/EP2017/070827
§ 371 (c)(1),
(2) Date: Mar. 8, 2019

(87) PCT Pub. No.: WO2018/046269
PCT Pub. Date: Mar. 15, 2018

(65) Prior Publication Data
US 2019/0216980 A1    Jul. 18, 2019

(30) Foreign Application Priority Data
Sep. 8, 2016    (EP) .................................... 16187904

(51) Int. Cl.
*B33Y 10/00*    (2015.01)
*B33Y 70/00*    (2020.01)
(Continued)

(52) U.S. Cl.
CPC ........... *A61L 27/446* (2013.01); *A61L 27/025* (2013.01); *A61L 27/18* (2013.01); *A61L 27/56* (2013.01);
(Continued)

(58) Field of Classification Search
CPC ....... B29C 64/153; B33Y 10/00; B33Y 70/00; B33Y 80/00
See application file for complete search history.

(56) References Cited

U.S. PATENT DOCUMENTS

| 4,915,987 A | 4/1990 | Nara et al. |
| 6,403,219 B1 | 6/2002 | Liao |

(Continued)

FOREIGN PATENT DOCUMENTS

| CN | 1887364 A | 1/2007 |
| CN | 101319075 A | 12/2008 |

(Continued)

OTHER PUBLICATIONS

Oct. 27, 2020—(RU) Request for Substantive Examination—App 2019109723/04018657—Eng Tran.

(Continued)

*Primary Examiner* — Nahida Sultana
(74) *Attorney, Agent, or Firm* — Banner & Witcoff, Ltd.

(57) ABSTRACT

The invention relates to a method for producing an implant which contains a composite powder comprising microstructured particles, obtainable by a method in which large polymer particles are bonded to small spherical calcium carbonate particles. Said calcium carbonate particles can be obtained by a method with the following steps: a) providing a calcium hydroxide suspension, b) introducing carbon dioxide or a carbon dioxide-containing gas mixture into the suspension from step a), and c) separating the calcium (Continued)

Figure 1:
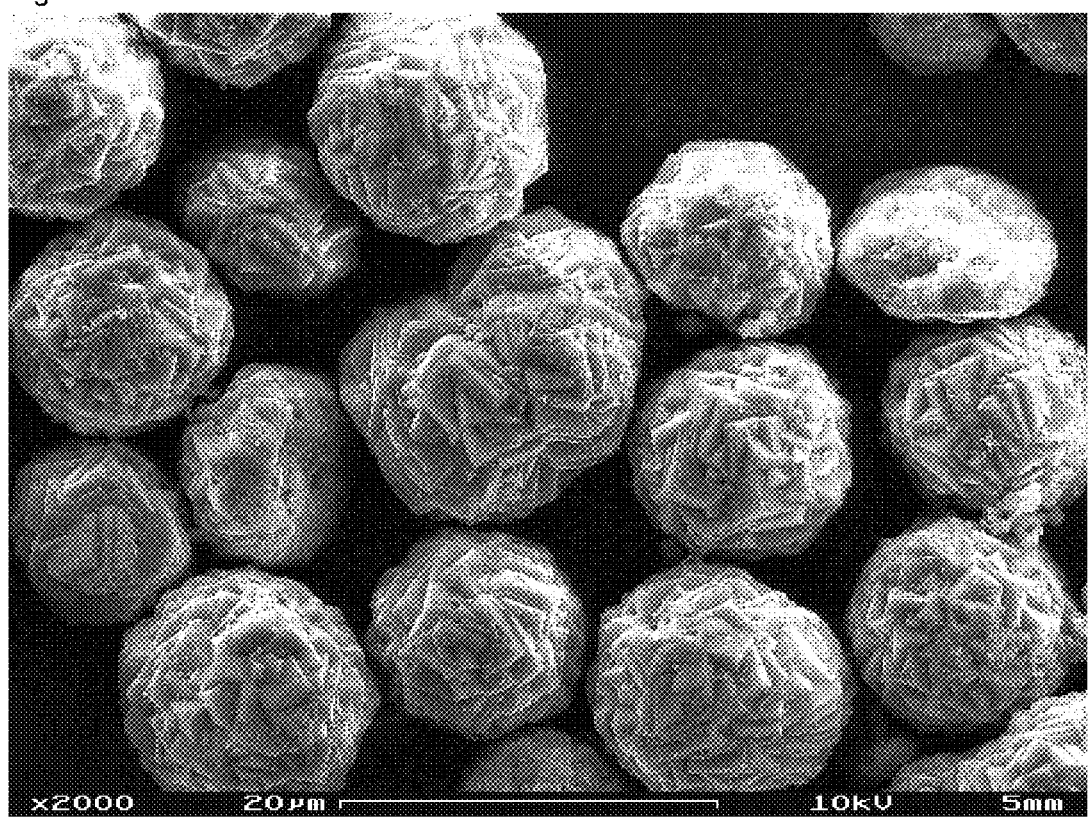

carbonate particles formed, while adding 0.3 wt.-% to 0.7 wt.-% of at least one amino trialkylene phosphonic acid.

20 Claims, 15 Drawing Sheets

(51) Int. Cl.
| | |
|---|---|
| B33Y 80/00 | (2015.01) |
| B29C 64/153 | (2017.01) |
| A61L 27/44 | (2006.01) |
| C01F 11/18 | (2006.01) |
| A61L 27/56 | (2006.01) |
| A61L 27/58 | (2006.01) |
| C08J 3/12 | (2006.01) |
| C08J 3/20 | (2006.01) |
| C09C 1/02 | (2006.01) |
| C09C 1/00 | (2006.01) |
| A61L 27/02 | (2006.01) |
| A61L 27/18 | (2006.01) |
| C08K 3/26 | (2006.01) |
| C08K 7/18 | (2006.01) |
| B29K 67/00 | (2006.01) |
| B29L 31/00 | (2006.01) |

(52) U.S. Cl.
CPC ............ *A61L 27/58* (2013.01); *B29C 64/153* (2017.08); *B33Y 10/00* (2014.12); *B33Y 70/00* (2014.12); *B33Y 80/00* (2014.12); *C01F 11/183* (2013.01); *C08J 3/124* (2013.01); *C08J 3/203* (2013.01); *C08K 3/26* (2013.01); *C08K 7/18* (2013.01); *C09C 1/0081* (2013.01); *C09C 1/021* (2013.01); *B29K 2067/046* (2013.01); *B29K 2995/006* (2013.01); *B29L 2031/7532* (2013.01); *C01P 2004/32* (2013.01); *C01P 2004/51* (2013.01); *C01P 2004/61* (2013.01); *C01P 2004/62* (2013.01); *C08J 2367/04* (2013.01); *C08K 2003/265* (2013.01); *C08K 2201/003* (2013.01); *C08K 2201/005* (2013.01)

(56) References Cited

U.S. PATENT DOCUMENTS

| | | | |
|---|---|---|---|
| 8,906,996 B2 * | 12/2014 | Vucak | C08K 3/26 524/425 |
| 9,593,244 B2 | 3/2017 | Gane et al. | |
| 9,707,734 B2 * | 7/2017 | Vucak | C09C 1/025 |
| 10,470,885 B2 | 11/2019 | Bake et al. | |
| 10,905,740 B2 | 2/2021 | Petrak et al. | |
| 2013/0190441 A1 | 7/2013 | Vucak et al. | |
| 2014/0004348 A1* | 1/2014 | Vucak | C09C 1/025 428/403 |
| 2014/0319412 A1 | 10/2014 | Gane et al. | |
| 2015/0225568 A1 | 8/2015 | Gane et al. | |
| 2017/0369695 A1 | 12/2017 | Gantenbein et al. | |
| 2019/0211179 A1* | 7/2019 | Vucak | B33Y 70/00 |

FOREIGN PATENT DOCUMENTS

| | | |
|---|---|---|
| CN | 102 247 624 A | 11/2011 |
| CN | 104910609 A | 9/2015 |
| CN | 105246518 A | 1/2016 |
| DE | 42 44 254 A1 | 7/1993 |
| EP | 0 523 372 A1 | 1/1993 |
| EP | 3488875 A1 | 5/2019 |
| GB | 2527492 A | 12/2015 |
| JP | S6283029 A | 4/1987 |
| JP | 2013531515 A | 8/2013 |
| JP | 2014508840 | 4/2014 |
| JP | 2015536726 A | 12/2015 |
| RU | 2519037 C2 | 6/2010 |
| RU | 2585785 C1 | 5/2013 |
| RU | 2520452 C2 | 7/2013 |
| RU | 2012101307 A | 7/2013 |
| RU | 148729 U1 | 9/2014 |
| WO | 2006/050119 A2 | 5/2006 |
| WO | 2012/013349 A2 | 2/2012 |
| WO | 2012/126600 A2 | 9/2012 |
| WO | 2012126600 A2 | 9/2012 |
| WO | 2015067522 A1 | 5/2015 |

OTHER PUBLICATIONS

Aug. 3, 2021—(JP) Notice of Reasons for Refusal—App 2019-513360 and Eng. Tran.
Oct. 11, 2017—PCT/EP2017/070827—WO.
Oct. 11, 2017—PCT/EP2017/070827—ISR.
Mar. 26, 2021—(CN) First Office Action—App 201780068435.1—Eng Tran.
"Pigment Coating and Surface Sizing of Paper,"—Esa Lehtinen, 3 pages.
Feb. 10, 2017—(EP) Search Report—App 16187904.4—Eng Tran.
Jan. 27, 2021—(RU) 2nd Examination Office Action—App 2019109723/0408657—machine English translation.

\* cited by examiner

METHOD FOR PRODUCING AN IMPLANT USING A CALCIUM CARBONATE-CONTAINING COMPOSITE POWDER COMPRISING MICROSTRUCTURED PARTICLES

CROSS-REFERENCE TO RELATED APPLICATIONS

This application is a U.S. National Stage application under 35 U.S.C. § 371 of International Application PCT/EP2017/070827 (published as WO 2018/046269 A1), filed Aug. 17, 2017, which claims the benefit of priority to Application EP 16187904.4, filed Sep. 8, 2016. Benefit of the filing date of each of these prior applications is hereby claimed. Each of these prior applications is hereby incorporated by reference in its entirety.

The present invention relates to an implant comprising a composite powder containing calcium carbonate including microstructured particles, in particular implants obtained by selective laser sintering, for instance those for use in the field of neuro, oral, maxillary, facial, ear, nose and throat surgery as well as hand, foot, thorax, costal and shoulder surgery.

The invention does not relate to the preparation of the starting material for the implant, nor to the use for purposes other than the production of an implant, especially one that is prepared for use in the field of neuro, oral, maxillary, facial, ear, nose and throat surgery as well as hand, foot, thorax, costal and shoulder surgery.

Calcium carbonate, $CaCO_3$, is a calcium salt of the carbonic acid which today is in use in various fields of daily life. It is used especially as an additive or modifier in paper, dyes, plastics, inks, adhesives and pharmaceuticals. In plastics, calcium carbonate preferentially serves as filler to replace the comparatively expensive polymer.

Also, composite materials are known already and denote a material consisting of two or more bonded materials which has material properties other than its individual components. Concerning the properties of the composite materials, the material properties and the geometry of the components are important. In particular, effects of size frequently play a role. The bonding is usually made by material bond or form fit or by a combination of both.

Further, also microstructured composite particles containing calcium salts, especially calcium carbonate, are known per se already.

For example, WO 2012/126600 A2 discloses microstructured composite particles obtainable by a method in which large particles are bonded to small particles, wherein
  the large particles have a mean particle diameter within the range from 0.1µ to 10 mm,
  the mean particle diameter of the small particles is no more than ⅒ of the mean particle diameter of the large particles,
  the large particles comprise at least one polymer,
  the small particles comprise calcium carbonate,
  the small particles are disposed on the surface of the large particles and/or are distributed non-homogeneously within the large particles,
wherein the small particles comprise precipitated calcium carbonate particles having a mean particle size within the range from 0.01 µm to 1.0 mm.

Further, WO 2012/126600 A2 describes microstructured composite particles obtainable by a method in which large particles are bonded to small particles, wherein
  the large particles have a mean particle diameter within the range from 0.1 µm to 10 mm,
  the mean particle diameter of the small particles is no more than ⅒ of the mean particle diameter of the large particles,
  the large particles comprise at least one polymer,
  the small particles comprise at least one calcium salt,
  the small particles are disposed on the surface of the large particles and/or are non-homogeneously distributed within the large particles,
wherein the large particles comprise at least one resorbable polyester having a number average molecular weight within the range from 500 g/mol to 1,000,000 g/mol.

The composite particles shown in WO 2012/126600 A2 are intended to be suited mainly as an additive, especially as a polymer additive, as an admixture or starting material for the production of components, for use in medical engineering and/or in microtechnology and/or for the production of foamed objects. The method of selective laser sintering (SLM method) is mentioned inter alia in the document.

However, for selective laser sintering more properly suited materials are desired. One drawback of the composite particles of WO 2012/126600 A2 especially is the poor flowability thereof which can only partially be reduced even when flowing aids are used. Additions of said flowing aids are not beneficial, above all, to the production of implants, as they usually have a detrimental effect on the properties of the resulting implant, especially on its biocompatibility and biodegradability. Further, transportation in the laser sintering plant is impeded by the poor flowability.

When producing components by laser sintering making use of the materials of WO 2012/126600 A2, the following additional problems will arise. Although ground composite particles can be sintered, the surface quality and surface finish as well as the component density of the resulting components are not fully satisfactory. Especially better shrinking behavior and better dimensional stability of the resulting components as well as better heat conductivity outside the laser-treated area would be desirable. Moreover, a more efficient production process of components would be desirable. In particular, an improvement for implants, especially for the field of neuro, oral, maxillary, facial, ear, nose and throat surgery as well as of hand, foot, thorax, costal and shoulder surgery would be desirable.

Against this background, it is the object of the present invention to make available a better implant than before. Especially a material exhibiting improved laser sintering properties should be used for an implant, which material in particular has an improved flowability, during laser sintering enables components of improved surface quality and surface finish as well as improved component density to be produced and shows especially better shrinking behavior and improved dimensional stability of the resulting components as well as better heat conductivity outside the laser-treated area. In addition, a more efficient production process of such implants is desired.

This object as well as further objects which are not concretized but can be directly derived from the foregoing context are achieved by providing an implant made from a composite powder including micro structured particles including all features of the present claim 1. The subclaims related back to claim 1 describe especially expedient variants. The use claim relates to an especially expedient application of the composite powder according to the invention for producing an implant, especially for the field of neuro, oral, maxillary, facial, ear, nose and throat surgery as well as of hand, foot, thorax, costal and shoulder surgery. Furthermore, an especially advantageous implant is protected which is obtained by selective laser sintering in a composition containing said composite powder and which is especially configured as an implant for applications in the field of neuro, oral, maxillary, facial, ear, nose and throat surgery as well as of hand, foot, thorax, costal and shoulder surgery.

By providing a composite powder having microstructured particles obtainable by a method of bonding large particles to small particles, wherein
- the large particles have an average particle diameter in the range from 0.1 µm to 10 mm,
- the large particles comprise at least one polymer,
- the small particles are arranged on the surface of the large particles and/or are distributed non-homogeneously within the large particles,
- the small particles comprise spherical precipitated calcium carbonate particles having an average diameter in the range from 0.05 µm to 50.0 µm, preferably in the range from 2.5 µm to 30.0 µm,
- wherein the spherical calcium carbonate particles are obtained by a method in which
  - a. a calcium hydroxide suspension is provided,
  - b. carbon dioxide or a gas mixture containing carbon dioxide is introduced into the suspension from step a. and
  - c. the calcium carbonate particles formed are separated,
- wherein 0.3% by weight to 0.7% by weight of at least one aminotrialkylene phosphonic acid is further added, it is possible in a not readily predictable way to make available a calcium carbonate-containing composite powder with improved properties, which are particularly suitable for use in laser sintering processes. The composite powder according to the invention has an improved flowability and enables the production of components with improved surface quality and surface condition as well as improved component density during laser sintering. At the same time, the resulting components show better shrinkage behavior and improved dimensional stability. Furthermore, a better thermal conductivity outside the laser-treated area can be observed.

Moreover, said composite powder allows for more efficient production of implants, especially according to the laser sintering method. The melt flow of the melt obtainable using the composite powder according to the invention is significantly increased (enhanced). The composite powder according to the invention can be better processed especially according to the SLM method, compared to conventional materials, and enables a significantly better layer structure in the SLM method. The components obtainable according to the SLM method using the composite powder according to the invention excel by extremely high quality and, compared to components produced according to the SLM method using conventional materials, show definitely fewer defects, an increased component density, preferably higher than 95%, especially higher than 97%, as well as less porosity. At the same time, the content of degradation products in the resulting components is significantly lower and the cell compatibility of the components is extremely high.

The other properties of the implants obtainable in this way are excellent, too. The implants show very good mechanical properties as well as excellent pH stability. At the same time, the biocompatibility of the products is significantly enhanced. Comparable products are not obtainable when using the pure polymers, particularly since respective polymer powders which might be processed according to the SLM method are not known.

It is another advantage of the present invention that the properties of said composite powder, especially the flow properties of the composite powder, can be specifically controlled and adjusted by the quantity used and the properties of the large and small particles, especially by the properties of the calcium carbonate particles, above all by the particle size of the calcium carbonate particles, as well as by the quantity of the calcium carbonate particles. Moreover, by sizing the composite powder, especially the calcium carbonate content of the composite powder and the flow properties of the composite powder can be varied and specifically adapted to the respective application.

Especially in combination with polylactide as polymer, the following advantages result according to the invention.

Using said composite powder, degradable implants having controllable absorption kinetics and adjustable mechanical properties can be produced. Polylactides which are preferably contained in the composite powder are biodegradable polymers on the basis of lactic acid. In the organism, polylactides are degraded by hydrolysis. Calcium salts, especially calcium phosphate and calcium carbonate, are mineral materials based on calcium and are degraded in the body by the natural regeneration process of the bone. Calcium carbonate has the particularly advantageous property to buffer the acidic milieu which may be toxic to bone cells when the polylactides are degraded. As compared to calcium phosphate (pH 4), calcium carbonate buffers already at a pH value of about 7, i.e. close to the physiological value of 7.4. The time until complete degradation can be adapted via the length of molecular chains and the chemical composition of the polymer, especially of the polylactide. This is similarly possible for the mechanical properties of the polymer.

Said composite powder may be processed to form implant structures with the aid of the generative production method of Selective Laser Melting (SLM). Here, a specific adaptation of the material and the production method to each other and to the medical requirements is possible. The use of the generative production and the accompanying freedom of geometry offers the option to provide the implant with an internal and open pore structure corresponding to the surgeon's requests which ensures continuous supply of the implant. Moreover, generatively individually adapted implants as required for supplying large-area bone defects in the craniofacial area can be quickly and economically manufactured. The advantage of the composite powder according to the invention for processing by means of SLM especially resides in the fact that the polymer can be melted by laser radiation at relatively low temperatures, preferably less than 300° C., and the calcium carbonate particles remain thermally stable at said temperatures. By customized synthesis of said composite powder, the calcium carbonate particles thus can be homogeneously embedded within the entire volume of the implant in a matrix of polylactide without thermal damage by the laser radiation. The strength of the implant is determined, on the one hand, by the polylactide matrix and, on the other hand, by the morphology of the calcium carbonate particles, and preferably also by the mixing ratio of the components used. Moreover, the implants are bioactive, as they actively stimulate the surrounding bone tissue to osteogenesis and replacement of the skeleton structure (implant) via the selection of material and the subsequent coating with a growth-stimulating protein (rhBMP-2).

The substantial benefits of the implants made of said composite powder, generatively produced by means of SLM especially are as follows:
- The use of biodegradable osteoconductive materials actively stimulates the bone to grow through the implant and, even for large-area defects, achieves complete degradation while bone forms completely newly in the bone defect to be repaired. Due to the interconnecting pore structure, the BMP coating can be active in the entire "volume" of the implant.

Sprouting of bone tissue: Introduction of a proper pore structure favors sprouting of new bone tissue into the implant. The generative production process helps to introduce a defined pore structure into the components in a reproducible manner The suggested solution further offers the advantage to prevent medical complications of long-term implants at best, to increase at best the patient's wellbeing by avoiding permanent foreign body sensation, and—above all for children and young persons—to realize at best a "growing" implant.

Optimum buffering: By the use of calcium carbonates, the acid degradation of the polylactide material is buffered already at a pH value of about 7 so that the forming acid milieu in the environment of the implant and thus inflammatory or cytotoxic action can be prevented. Moreover, degradation processes of the polymer, especially of the lactic acid polymer, are suppressed at best.

High strength: The SLM process produces a completely fused compound and thus high component density and strength, thus allowing even large-area defects to be repaired by individually adapted implants made from biodegradable material and having an open pore structure.

Accordingly, the subject matter of the present invention is a composite powder comprising microstructured particles (composite powder) in an implant, the composite powder being obtainable by a method in which large particles are bonded to small particles.

In the present invention, the term "microstructure" refers to the microscopic properties of a material. These include, inter alia, the resolvable fine structure and the structure. In liquids as well as in gases, the latter are not provided. Here, the individual atoms or molecules are in a disordered state. Amorphous solids mostly have a structural short-range order in the area of the neighboring atoms, but no long-range order. Crystalline solids, on the other hand, have an ordered grid structure not only in the short-range area but also in the long-range area.

Within the scope of the present invention, the large particles comprise at least one polymer which basically is not subject to any further restrictions. However, it is preferably a thermoplastic polymer, appropriately a biopolymer, a rubber, especially natural rubber or synthetic rubber, and/or a polyurethane.

The term "thermoplastic polymer" in this context refers to a plastic which can be (thermoplastically) deformed within a specific temperature range, preferably within the range from 25° C. to 350° C. This operation is reversible, i.e. it can be repeated any number of times by cooling and reheating to the molten state, unless the so-called thermal decomposition of the material starts by overheating. By this feature, thermoplastic polymers differ from the thermosetting plastics and elastomers.

The term "biopolymer" denotes a material consisting of biogenic raw materials (renewable raw materials) and/or being biodegradable (biogenic and/or biodegradable polymer). This term thus covers bio-based biopolymers which are biodegradable or not, as well as petroleum-based polymers which are biodegradable. Thus, a delimitation is made against the conventional petroleum-based materials and plastics which are not biodegradable such as e.g. polyethylene (PE), polypropylene (PP) and polyvinylchloride (PVC).

The term "rubber" denotes high-molecular non-cross-linked polymeric material having rubber-elastic properties at room temperature (25° C.). At higher temperatures or under the influence of deforming forces, rubber shows increasingly viscous flow and thus enables to be reformed under appropriate conditions.

Rubber-elastic behavior is characterized by a relatively low shear modulus with rather low temperature dependency. It is caused by changes of entropy. By stretching, the rubber-elastic material is forced to adopt a more ordered configuration resulting in a decrease of entropy. After removing the force, the polymers therefore return to their original position and the entropy increases again.

The term "polyurethane" (PU, DIN abbreviation: PUR) denotes a plastic or synthetic resin which is formed by the poly-addition reaction of diols or polyols with poly-isocyanates. The urethane group is a typical example of a polyurethane.

Within the scope of the present invention, it is especially preferred to use thermoplastic polymers. Especially suited polymers include the following polymers: acrylonitrile-ethylene-propylene-(diene)-styrene copolymer, acrylonitrile-methacrylate copolymer, acrylonitrile-methyl methacrylate copolymer, acrylonitrile-chlorinated polyethylene-styrene copolymer, acrylonitrile-butadiene-styrene copolymer, acrylonitrile-ethylene-propylene-styrene copolymer, aromatic polyesters, acrylonitrile-styrene-acrylic ester copolymer, butadiene-styrene copolymer, cellulose acetate, cellulose aceto butyrate, cellulose aceto propionate, hydrated cellulose, carboxymethyl cellulose, cellulose nitrate, cellulose propionate, cellulose triacetate, polyvinyl chloride, ethylene-acrylic acid copolymer, ethylene-butyl acrylate copolymer, ethylene-chlorotrifluoroethylene copolymer, ethylene-ethyl acrylate copolymer, ethylene-methacrylate copolymer, ethylene-methacrylic acid copolymer, ethylene-tetrafluoroethylene copolymer, ethylene-vinyl alcohol copolymer, ethylene-butene copolymer, ethyl cellulose, polystyrene, poly fluoroethylene propylene, methyl methacrylate-acrylonitrile-butadiene-styrene copolymer, methyl methacrylate-butadiene-styrene copolymer, methyl cellulose, polyamide 11, polyamide 12, polyamide 46, polyamide 6, polyamide 6-3-T, polyamide 6-terephthalic acid copolymer, polyamide 66, polyamide 69, polyamide 610, polyamide 612, polyamide 6I, polyamide MXD 6, polyamide PDA-T, polyamide, polyaryl ether, polyaryl ether ketone, polyamide imide, polyaryl amide, polyamine bismaleimide, polyarylates, polybutene-1, polybutyl acrylate, polybenzimidazole, polybismaleimide, polyoxadiazo benzimidazole, polybutylene terephthalate, polycarbonate, polychlorotrifluoroethylene, polyethylene, polyester carbonate, polyaryl ether ketone, polyetherether ketone, polyether imide, polyether ketone, polyethylene oxide, polyaryl ether sulfone, polyethylene terephthalate, polyimide, polyisobutylene, polyisocyanurate, polyimide sulfone, polymethacryl imide, polymethacrylate, poly-4-methylpentene-1, polyacetal, polypropylene, polyphenylene oxide, polypropylene oxide, polyphenylene sulfide, polyphenylene sulfone, polystyrene, polysulfone, polytetrafluoroethylene, polyurethane, polyvinyl acetate, polyvinyl alcohol, polyvinyl butyral, polyvinyl chloride, polyvinylidene chloride, polyvinylidene fluoride, polyvinyl fluoride, polyvinyl methyl ether, polyvinyl pyrrolidone, styrene-butadiene copolymer, styrene-isoprene copolymer, styrene-maleic acid anhydride copolymer, styrene-maleic acid anhydride-butadiene copolymer, styrene methyl methacrylate copolymer, styrene methyl styrene copolymer, styrene acrylonitrile copolymer, vinyl chloride ethylene copolymer, vinyl chloride methacrylate copolymer, vinyl chloride-maleic acid anhydride copolymer, vinyl chloride maleimide copolymer, vinyl chloride-methyl methacrylate copolymer, vinyl chloride octyl acrylate copolymer, vinyl chloride vinyl acetate copolymer, vinyl chloride vinylidene chloride copolymer and vinyl chloride vinylidene chloride-acrylonitrile copolymer.

Further, also the use of the following rubbers is especially advantageous: naturally occurring polyisoprene, especially cis-1,4-polyisoprene (natural rubber; NR) and trans-1,4-polyisoprene (gutta-percha), primarily natural rubber; nitrile rubber (copolymer of butadiene and acrylonitrile); poly (acrylonitrile-co-1,3-butadiene; NBR; so-called Buna N-rubber); butadiene rubber (polybutadiene; BR); acrylic rubber (polyacrylic rubber; ACM, ABR); fluorine rubber (FPM); styrene-butadiene rubber (copolymer of styrene and butadiene; SBR); styrene-isoprene-butadiene rubber (copolymer of styrene, isoprene and butadiene; SIBR); polybutadiene; synthetic isoprene rubber (polyisoprene; IR), ethylene-propylene rubber (copolymer of ethylene and propylene; EPM); ethylene-propylene-diene rubber (terpolymer of ethylene, propylene and a diene component; EPDM); butyl rubber (copolymer of isobutylene and isoprene; IIR); ethylene-vinyl acetate rubber (copolymer of ethylene and vinyl acetate; EVM); ethylene-methacrylate rubber (copolymer of ethylene and methacrylate; AEM); epoxy rubber such as polychloromethyl oxirane (epichlorohydrin polymer; CO), ethylene oxide (oxirane)-chloromethyl oxirane (epichlorohydrin polymer; ECO), epichlorohydrin-ethylene oxide-allyl glycidyl ether terpolymer (GECO), epichlorohydrin-allyl glycidyl ether copolymer (GCO) and propylene oxide-allyl glycidyl ether copolymer (GPO); polynorbornene rubber (polymer of bicyclo[2.2.1] hept-2-en (2-norbornene); PNR); polyalkenylene (polymer of cycloolefins); silicone rubber (Q) such as silicone rubber but with methyl substituents at the polymer chain (MQ; e.g. dimethyl polysiloxane), silicone rubber with methyl vinyl and vinyl substituent groups at the polymer chain (VMQ), silicone rubber with phenyl and methyl substituents at the polymer chain (PMQ), silicone rubber with fluorine and methyl groups at the polymer chain (FMQ), silicone rubber with fluorine, methyl and vinyl substituents at the polymer chain (FVMQ); polyurethane rubber; polysulfide rubber; halogen butyl rubber such as bromine butyl rubber (BIIR) and chlorine butyl rubber (CIIR); chlorine polyethylene (CM); chlorine sulfonyl polyethylene (CSM); hydrated nitrile rubber (HNBR); and polyphosphazene.

Especially preferred nitrile rubbers include statistic terpolymers of acrylonitrile, butadiene and a carboxylic acid such as methacrylic acid. In this context, the nitrile rubber preferably comprises the following main components, based on the total weight of the polymer: 15.0 wt.-% to 42.0 wt.-% of acrylonitrile polymer; 1.0 wt.-% to 10.0 wt.-% of carboxylic acid and the remainder is mostly butadiene (e.g. 38.0 wt.-% to 75.0 wt.-%). Typically, the composition is: 20.0 wt.-% to 40.0 wt.-% of acrylonitrile polymer, 3.0 wt.-% to 8.0 wt.-% of carboxylic acid and 40.0 wt.-% to 65.0 wt.-% or 67.0 wt.-% are butadiene. Especially preferred nitrile rubbers include a terpolymer of acrylonitrile, butadiene and a carboxylic acid in which the content of acrylonitrile is less than 35.0 wt.-% and the content of carboxylic acid is less than 10.0 wt.-%, with the content of butadiene corresponding to the remainder. Even more preferred nitrile rubbers may comprise the following quantities: 20.0 wt.-% to 30.0 wt.-% of acrylonitrile polymer, 4.0 wt.-% to 6.0 wt.-% of carboxylic acid and the remainder is butadiene for the most part The use of nitrogenous polymers, especially of polyamides, is especially favorable within the scope of the present invention. Especially preferred are polyamide 11, polyamide 12, polyamide 46, polyamide 6, polyamide 6-3-T, polyamide 6-terephthalic acid copolymer, polyamide 66, polyamide 69, polyamide 610, polyamide 612, polyamide 6I, polyamide MXD 6 and/or polyamide PDA-T, especially polyamide 12.

Moreover, also ultrahigh-molecular polyethylenes (UHMWPE) are especially beneficial to the purposes of the present invention, especially those having an average molar mass of more than 1000 kg/mol, preferably more than 2000 kg/mol, especially preferred more than 3000 kg/mol, especially more than 5000 kg/mol. The average molecular weight favorably is no more than 10000 kg/mol. The density of especially suited ultrahigh-molecular polyethylenes is within the range from 0.94-0.99 g/cm$^3$. The crystallinity of especially suited ultrahigh-molecular polyethylenes is within the range from 50% to 90%. The tensile strength of especially suited ultrahigh-molecular polyethylenes is within the range from 30 N/mm$^2$ to 50 N/mm$^2$. The tensile E modulus of especially suited ultrahigh-molecular polyethylenes is within the range from 800 N/mm$^2$ to 2700 N/mm$^2$. The melting range of especially suited ultrahigh-molecular polyethylenes is within the range from 135° C. to 155° C.

Furthermore, also the use of resorbable polymers is especially expedient. The term "resorption" (From Latin: resorbere="to absorb") is understood to be the absorption of matter in biological systems, especially into the human organism. Of current interest are especially those materials which can be used to produce resorbable implants.

Resorbable polymers especially preferred according to the invention comprise repeated units of lactic acid, hydroxybutyric acid and/or glycolic acid, of preference of lactic acid and/or glycolic acid, especially of lactic acid. Polylactic acids are especially preferred.

By "polylactic acid" (polylactides) polymers are understood which are structured of lactic acid units. Said polylactic acids are usually prepared by condensation of lactic acids but are also obtained during ring-opening polymerization of lactides under suitable conditions.

Resorbable polymers especially suited according to the invention include poly(glycolide-co-L-lactide), poly(L-lactide), poly(L-lactide-co-ε-caprolactone), poly(L-lactide-co-glycolide), poly(L-lactide-co-D,L-lactide), poly(D,L-lactide-co-glycolide) as well as poly(dioxanone), wherein lactic acid polymers, especially poly-D-, poly-L- or poly-D,L-lactic acids, above all poly-L-lactic acids (PLLA) and poly-D,L-lactic acids, are especially preferred according to the invention, wherein especially the use of poly-L-lactic acids (PLLA) is extraordinarily advantageous.

In accordance with the invention, poly-L-lactic acid (PLLA) preferably has the following structure

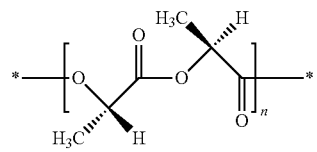

wherein n is an integer, preferably larger than 10.

Poly-D,L-lactic acid preferably has the following structure

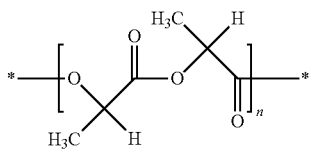

wherein n is an integer, preferably larger than 10.

Lactic acid polymers suited for the purpose of the present invention are, for example, commercially available by Evonik Nutrition & Care GmbH under the brand names Resomer® GL 903, Resomer® L 206 S, Resomer® L 207 S, Resomer® R 208 G, Resomer® L 209 S, Resomer® L 210, Resomer® L 210 S, Resomer® LC 703 S, Resomer® LG 824 S, Resomer® LG 855 S, Resomer® LG 857 S, Resomer® LR 704 S, Resomer® LR 706 S, Resomer® LR 708, Resomer® LR 927 S, Resomer® RG 509 S and Resomer® X 206 S.

Resorbable polymers especially beneficial to the purposes of the present invention, which preferably are resorbable polyesters, preferably lactic acid polymers, especially preferred poly-D-, poly-L- or poly-D,L-lactic acids, especially poly-L-lactic acids, have a number average molecular weight (Mn), preferably determined by gel permeation chromatography against narrowly distributed polystyrene standards or by final group titration, of more than 500 g/mol, preferably more than 1,000 g/mol, especially preferred more than 5,000 g/mol, appropriately more than 10,000 g/mol, in particular more than 25,000 g/mol. On the other hand, the number average of preferred resorbable polymers is less than 1,000,000 g/mol, appropriately less than 500,000 g/mol, favorably less than 100,000 g/mol, especially not exceeding 50,000 g/mol. A number average molecular weight within the range from 500 g/mol to 50,000 g/mol has particularly proved its worth within the scope of the present invention.

The weight average of the molecular weight (Mw) of preferred resorbable polymers, which preferably are resorbable polyesters, favorably lactic acid polymers, especially preferred poly-D-, poly-L- or poly-D,L-lactic acids, especially poly-L-lactic acids, preferably determined by gel permeation chromatography against narrowly distributed polystyrene standards, ranges of preference from 750 g/mol to 5,000,000 g/mol, preferably from 750 g/mol to 1,000,000 g/mol, especially preferred from 750 g/mol to 500,000 g/mol, especially from 750 g/mol to 250,000 g/mol, and the polydispersity of said polymers favorably ranges from 1.5 to 5.

The inherent viscosity of especially suited resorbable polymers, which preferably are lactic acid polymers, especially preferred poly-D-, poly-L- or poly-D,L-lactic acids, in particular poly-L-lactic acids, measured in chloroform at 25° C. with 0.1% of polymer concentration, ranges from 0.3 dl/g to 8.0 dl/g, of preference from 0.5 dl/g to 7.0 dl/g, especially preferred from 0.8 dl/g to 2.0 dl/g, especially from 0.8 dl/g to 1.2 dl/g.

Further, the inherent viscosity of especially suited resorbable polymers, which preferably are lactic acid polymers, especially preferred poly-D-, poly-L- or poly-D,L-lactic acids, especially poly-L-lactic acids, measured in hexafluoro-2-propanol at 30° C. with 0.1% polymer concentration, ranges from 1.0 dl/g to 2.6 dl/g, especially from 1.3 dl/g to 2.3 dl/g.

Within the scope of the present invention, moreover polymers, favorably thermoplastic polymers, of preference lactic acid polymers, especially preferred poly-D-, poly-L- or poly-D,L-lactic acids, especially poly-L-lactic acids, having a glass transition temperature of more than 20° C., favorably more than 25° C., preferably more than 30° C., especially preferred more than 35° C., especially more than 40° C., are extremely advantageous. Within the scope of an extraordinarily preferred embodiment of the present invention, the glass transition temperature of the polymer is within the range from 35° C. to 70° C., favorably within the range from 55° C. to 65° C., especially within the range from 60° C. to 65° C.

Furthermore, polymers, favorably thermoplastic polymers, of preference lactic acid polymers, especially preferred poly-D-, poly-L- or poly-D,L-lactic acids, especially poly-L-lactic acids, which exhibit a melting temperature of more than 50° C., favorably of at least 60° C., preferably of more than 150° C., especially preferred within the range from 130° C. to 210° C., especially within the range from 175° C. to 195° C., are especially suited.

The glass temperature and the melting temperature of the polymer are preferably established by means of differential scanning calorimetry, abbreviated to DSC. In this context, the following procedure has proved to be successful:

Carrying out the DSC measurement under nitrogen on a Mettler-Toledo DSC 30S. Calibration is preferably carried out with indium. The measurements are preferably carried out under dry oxygen-free nitrogen (flow rate: preferably 40 ml/min). The sample weight is preferably selected to be between 15 mg and 20 mg. The samples are initially heated from 0° C. to preferably a temperature above the melting temperature of the polymer to be tested, then cooled down to 0° C. and a second time heated from 0° C. to said temperature at a heating rate of 10° C./min.

Polyamides, UHMWPE as well as resorbable polymers, above all resorbable polyesters such as poly butyric acid, polyglycolic acid (PGA), lactic acid polymers (PLA) and lactic acid copolymers are especially preferred as thermoplastic polymers, with lactic acid polymers and lactic acid copolymers, especially poly-L-lactide, poly-D,L-lactide, copolymers of D,L-PLA and PGA, have particularly proved their worth in the invention.

For the objectives of the present invention, especially the following polymers are particularly suited:
1) Poly-L-lactide (PLLA), preferably having an inherent viscosity within the range from 0.5 dl/g to 2.5 dl/g, favorably within the range from 0.8 dl/g to 2.0 dl/g, especially within the range from 0.8 dl/g to 1.2 dl/g (each time measured in 0.1% chloroform at 25° C.), preferably having a glass transition temperature ranging from 60° C. to 65° C., further preferred having a melting temperature ranging from 180° C. to 185° C., moreover preferably ester-terminated;
2) Poly(D,L-lactide), preferably with an inherent viscosity within the range from 1.0 dl/g to 3.0 dl/g, favorably within the range from 1.5 dl/g to 2.5 dl/g, especially within the range from 1.8-2.2 dl/g (each time measured in 0.1% chloroform at 25° C.), preferably having a glass transition temperature ranging from 55° C. to 60° C.,
wherein the best results are obtained using a poly-L-lactide which preferably has an inherent viscosity within the range from 0.5 dl/g to 2.5 dl/g, favorably within the range from 0.8 dl/g to 2.0 dl/g, especially within the range from 0.8 dl/g to 1.2 dl/g (each time measured in 0.1% chloroform at 25° C.), preferably has a glass transition temperature ranging from 60° C. to 65° C., further preferred has a melting temperature ranging from 180° C. to 185° C. and moreover is preferably ester-terminated.

Within the scope of the present invention, the small particles (second material) that can be used to produce the composite powder in question comprise spherical precipitated calcium carbonate particles. In contrast to other known shapes in prior art, the calcium carbonate particles are not composed of needles, rhombohedra or scalenohedra (precipitated calcium carbonate; PCC) or irregularly shaped particles (ground calcium carbonate; GCC), but of spherical precipitated particles, which are mainly present in the form of individual pieces. However, smaller deviations from the perfect spherical shape are accepted as long as the properties of the particles, in particular their dispersibility, are not fundamentally altered. For example, the surface of the particles may occasionally show flaws or additional deposits.

In accordance with the invention, the term "spherical precipitated calcium carbonate particles" also includes fragments of spherical particles which are obtained, for example, by grinding the calcium carbonate. However, the proportion of the spherical fragments is preferably less than 95%, preferably less than 75%, particularly preferred less than 50%, particularly less than 25%, in each case relative to the total amount of spherical precipitated calcium carbonate.

The mean diameter of the spherical calcium carbonate particles is in the range from 0.05 µm to 50.0 µm, especially in the range from 2.5 µm to 30.0 µm. Here, the mean particle diameter is expediently more than 2.5 µm, favorably more than 3.0 µm, preferably more than 4.0 µm, expediently more than 5.0 µm, expediently more than 6.0 µm, preferably more than 7.0 µm, particularly preferred more than 8.0 µm, even more preferred more than 9.0 µm, especially preferred more than 10.0 µm, more preferably more than 11.0 µm, above all more than 12.0 µm, in particular more than 13.0 µm. Furthermore, the mean particle diameter should expediently be smaller than 30.0 µm, favorably smaller than 20.0 µm, preferably smaller than 18.0 µm, especially preferred smaller than 16.0 µm, in particular smaller than 14.0 µm.

In the context of the present invention, the mean diameter of the calcium carbonate particles is determined expediently by the evaluation of scanning electron microscope images (SEM images), whereby preferably only particles with a size of at least 0.01 µm are taken into account and a number average of preferably at least 20, particularly preferred of at least 40 particles is formed. Furthermore, sedimentation analysis methods have proved to be particularly effective, whereby the use of a Sedigraph 5100 (Micromeritics GmbH) is particularly advantageous in this context.

The size distribution of the calcium carbonate particles is expediently comparatively narrow and preferably such that at least 90.0% by weight of all calcium carbonate particles have a particle diameter in the range from average particle diameter −30% to average particle diameter +30%.

The form factor of the small particles, currently defined as the quotient of minimum particle diameter and maximum particle diameter, expediently is more than 0.90, especially preferred more than 0.95 for at least 90%, favorably for at least 95% of all particles. In this context, preferably only particles having a particle size within the range from 0.1 µm to 50.0 µm, in particular within the range from 0.1 µm to 30.0 µm are considered.

The calcium carbonate particles favorably further excel by a comparatively low water content. Based on their total weight, they expediently have a water content (residual moisture at 200° C.) not exceeding 5.0 wt.-%, preferably not exceeding 2.5 wt.-%, preferably not exceeding 1.0 wt.-%, especially preferred not exceeding 0.5 wt.-%, yet more preferred less than 0.4 wt.-%, expediently less than 0.3 wt.-%, favorably less than 0.2 wt.-%, especially within the range from >0.1 wt.-% to <0.2 wt.-%.

Within the present invention, the water content of the calcium salt particles, especially of the calcium carbonate particles, is established preferably by means of thermal gravimetry or by means of a rapid infrared drier, e.g. MA35 or MA45 by Sartorius or using a halogen moisture analyzer HB43 by Mettler, wherein the measurement is preferably carried out under nitrogen (nitrogen flow rate of preferably 20 ml/min) and expediently across the temperature range from 40° C. or less to 250° C. or more. Further, the measurement is preferably carried out at a heating rate of 10° C./min.

The specific surface area of the calcium carbonate particles is preferably less than 3.0 m$^2$/g, preferably less than 2.0 m$^2$/g, in particular less than 1.5 m$^2$/g. Further, the specific surface area is favorably greater than 0.25 m$^2$/g, preferably greater than 0.5 m$^2$/g, in particular greater than 0.75 m$^2$/g.

Within a particularly preferred variant of the present invention, the calcium carbonate particles, in particular the precipitated calcium carbonate particles, are preferably spherical and essentially amorphous. At this point, the term "amorphous" refers to those calcium carbonate modifications in which the atoms form an irregular pattern rather than an ordered structure, at least in part, and therefore only have a short-range order, but not a distant order. A distinction must be made in relation to crystalline modifications of the calcium carbonate, such as calcite, vaterite and aragonite, in which the atoms have both a short-range and a distant order.

Within the framework of this preferred variant of the present invention, however, the presence of crystalline components is not categorically excluded. Preferably, however, the proportion of crystalline calcium carbonate is less than 50% by weight, especially less than 30% by weight, particularly preferred less than 15% by weight, in particular less than 10% by weight. In the context of a particularly preferred variant of the present invention, the proportion of crystalline calcium carbonate is less than 8.0% by weight, preferably less than 6.0% by weight, expediently less than 4.0% by weight, particularly preferred less than 2.0% by weight, particularly preferred less than 1.0% by weight, in particular less than 0.5% by weight, based in each case on the total weight of the calcium carbonate.

For establishing the amorphous and the crystalline fractions, X-ray diffraction with an internal standard, preferably quartz, in combination with Rietveld refinement has proved to be especially useful.

Within the scope of this preferred embodiment of the present invention, the preferably amorphous calcium carbonate particles are favorably stabilized by at least one substance, especially at least one surface-active substance, which is preferably arranged on the surface of the preferably spherical calcium carbonate particles. "Surface-active substances" in the sense of the present invention expediently denote organic compounds which strongly enrich themselves from their solution at boundary surfaces (water/calcium carbonate particles) and thus reduce the surface tension, preferably measured at 25° C. For further details, reference is made to technical literature, especially to Römpp-Lexikon Chemie/publisher Jürgen Falbe; Manfred Regitz. Revised by Eckard Amelingmeier; Stuttgart, N.Y.; Thieme; Volume 2: Cm-G; 10$^{th}$ Edition (1997); keyword: "surface-active substances".

Of preference, the substance, especially the surface-active substance, has a molar mass of more than 100 g/mol, preferably more than 125 g/mol, especially more than 150 g/mol, and satisfies the formula R—X$_n$.

The remainder R stands for a remainder comprising at least 1, preferably at least 2, of preference at least 4, especially preferred at least 6, especially at least 8, carbon atoms, preferably for an aliphatic or cycloaliphatic remainder which may comprise further remainders X, where necessary, and which may have one or more ether links, where necessary.

The remainder X stands for a group which comprises at least on oxygen atom as well as at least one carbon atom, sulfur atom, phosphorus atom and/or nitrogen atom, preferably at least one phosphorus atom and/or at least one carbon atom. Especially preferred are the following groups:
carboxylic acid groups ~COOH,
carboxylate groups ~COO$^-$,
sulfonic acid groups ~SO$_3$H,
sulfonate groups ~SO$_3^-$,
hydrogen sulfate groups ~OSO$_3$H,
sulfate groups ~OSO$_3^-$,
phosphonic acid groups ~PO$_3$H$_2$,
phosphonate groups ~PO$_3$H$^-$, ~PO$_3^{2-}$,
amino groups ~NR$^1$R$^2$ as well as
ammonium groups ~N$^+$R$^1$R$^2$R$^3$,
especially carboxylic acid groups, carboxylate groups, phosphonic acid groups and phosphonate groups.

The remainders R$^1$, R$^2$ and R$^3$ in this context stand independently of each other for hydrogen or an alkyl group having 1 to 5 carbon atoms. One of the remainders R$^1$, R$^2$ and R$^3$ may also be a remainder R.

Preferred counter-ions for the aforementioned anions are metal cations, especially alkaline metal cations, preferably Na$^+$ and K$^+$, as well as ammonium ions.

Preferred counter-ions for the aforementioned cations are hydroxy ions, hydrogen carbonate ions, carbonate ions, hydrogen sulfate ions, sulfate ions and halide ions, especially chloride and bromide ions.

Symbol n preferably stands for an integer within the range from 1 to 20, preferably within the range from 1 to 10, in particular within the range from 1 to 5.

Substances especially suited for the purposes of the present invention comprise alkyl carboxylic acids, alkyl carboxylates, alkyl sulfonic acids, alkyl sulfonates, alkyl sulfates, alkyl ether sulfates having preferably 1 to 4 ethylene glycol ether units, fatty alcohol ethoxylates having preferably 2 to 20 ethylene glycol ether units, alkyl phenol ethoxylates, possibly substituted alkyl phosphonic acids, possibly substituted alkyl phosphonates, sorbitan fatty acid esters, alkyl poly glucosides, N-methyl glucamides, homopolymers and copolymers of the acrylic acid and the corresponding salt forms and block copolymers thereof.

A first group of especially advantageous substances are possibly substituted alkyl phosphonic acids, especially amino-tri-(methylene phosphonic acid), 1-hydroxy ethylene-(1,1-diphosphonic acid), ethylene diamine-tetra-(methylene phosphonic acid), hexamethylene diamine-tetra-(methylene phosphonic acid), diethylene triamine-penta-(methylene phosphonic acid), as well as possibly substituted alkyl phosphonates, especially of the afore-mentioned acids. Said compounds are known as multifunctional sequestration means for metal ions and stone inhibitors.

Furthermore, also homopolymers and copolymers, preferably homopolymers, of the acrylic acid as well as the corresponding salt forms thereof have especially proven themselves, in particular those having a weight average molecular weight within the range from 1,000 g/ to 10,000 g/mol.

Further, the use of block copolymers, preferably of double-hydrophilic block copolymers, especially of polyethylene oxide or polypropylene oxide, is especially appropriate.

The fraction of the preferably surface-active substances may basically be freely selected and specifically adjusted for the respective application. However, it is preferred to be within the range from 0.1 wt.-% to 5.0 wt.-%, especially within the range from 0.3 wt.-% to 1.0 wt.-%, based on the calcium carbonate content of the particles.

The preferably spherical, preferably amorphous calcium carbonate particles may be prepared in a way known per se, e.g. by hydrolysis of dialkyl carbonate or of alkylene carbonate in a solution comprising calcium cations.

The preparation of non-stabilized spherical calcium carbonate particles is described in detail e.g. in the patent application WO 2008/122358, the disclosure of which, especially relating to particularly expedient variants of the preparation of such non-stabilized spherical calcium carbonate particles, is explicitly incorporated here by reference.

The hydrolysis of the dialkyl carbonate or the alkylene carbonate is usefully carried out in the presence of a hydroxide.

Substances preferred for the purpose of the present invention which contain Ca$^{2+}$ ions are calcium halides, preferably CaCl$_2$, CaBr$_2$, especially CaCl$_2$, as well as calcium hydroxide. Within the scope of a first especially preferred embodiment of the present invention, CaCl$_2$ is used. In a further especially preferred embodiment of the present invention, Ca(OH)$_2$ is used.

Within the scope of the first especially preferred embodiment of the present invention, a dialkyl carbonate is used. Particularly suited dialkyl carbonates comprise 3 to 20, preferably 3 to 9, carbon atoms, especially dimethyl carbonate, diethyl carbonate, di-n-propyl carbonate, di-isopropyl carbonate, di-n-butyl carbonate, di-sec-butyl carbonate and di-tert-butyl carbonate, with dimethyl carbonate being extraordinarily preferred in this context.

In another especially preferred embodiment of the present invention, an alkylene carbonate is reacted. Especially expedient alkylene carbonates comprise 3 to 20, preferred 3 to 9, especially preferred 3 to 6 carbon atoms and include especially those compounds containing a ring of 3 to 8, preferably 4 to 6, especially 5 atoms having preferably 2 oxygen atoms and otherwise carbon atoms. Propylene carbonate (4-methyl-1,3-dioxolane) has especially proven itself in this context.

Alkaline metal hydroxides, especially NaOH and calcium hydroxide, have turned out to be especially suited hydroxides. Within the scope of the first especially preferred embodiment of the present invention, NaOH is used. Within the scope of another especially preferred embodiment of the present invention, Ca(OH)$_2$ is used.

Further, the molar ratio of Ca$^{2+}$, preferably of calcium chloride, to OH$^-$, preferably alkali metal hydroxide, in the reaction mixture is preferably higher than 0.5:1 and especially preferred within the range from >0.5:1 to 1:1, especially within the range from 0.6:1 to 0.9:1.

The molar ratio of Ca$^{2+}$, preferably of calcium chloride, to dialkyl carbonate and/or alkylene carbonate in the reaction mixture favorably is within the range from 0.9:1.5 to 1.1:1, especially preferred within the range from 0.95:1 to 1:0.95. Within the scope of a particularly expedient variant of the present invention, dialkyl carbonate and/or alkylene carbonate and $Ca^{2+}$, especially calcium chloride, are used in equimolar quantity.

Within a first particularly preferred variant of the present invention, it is not $Ca(OH)_2$ which is used as $OH^-$ source. The components for the reaction are favorably used in the following concentrations:
a) $Ca^{2+}$: >10 mmol/l to 50 mmol/l, preferably 15 mmol/l to 45 mmol/l, especially 17 mmol/l to 35 mmol/l;
b) dialkyl carbonate and/or
  alkylene carbonate: >10 mmol/l to 50 mmol/l, preferably 15 mmol/l to 45 mmol/l, especially 17 mmol/l to 35 mmol/l;
c) $OH^-$: 20 mmol/l to 100 mmol/l, preferably 20 mmol/l to 50 mmol/l, especially preferred 25 mmol/l to 45 mmol/l, in particular 28 mmol/l to 35 mmol/l.

The respective indicated concentrations relate to the concentrations of the given components in the reaction mixture.

Within a further especially preferred variant of the present invention, $Ca(OH)_2$, preferred limewater, especially saturated limewater, is used as $OH^-$ source. The components for the reaction are favorably used in the following concentrations:
a) $Ca(OH)_2$: >5 mmol/l to 25 mmol/l, preferably 7.5 mmol/l to 22.5 mmol/l, especially 8.5 mmol/l to 15.5 mmol/l;
b) dialkyl carbonate and/or
  alkylene carbonate: >5 mmol/l to 25 mmol/l, preferably 7.5 mmol/l to 22.5 mmol/l, especially 8.5 mmol/l to 15.5 mmol/l.

The respective indicated concentrations relate to the concentrations of the mentioned components in the reaction mixture.

The reaction of the components is preferably carried out at a temperature in the range from 15° C. to 30° C.

The actual size of the calcium carbonate particles can be controlled by supersaturation in a manner known per se.

The calcium carbonate particles precipitate from the reaction mixture under the above conditions.

The stabilization of the preferably amorphous calcium carbonate particles is carried out expediently by adding the preferably surface-active substance to the reaction mixture.

Said addition of the substance should not take place before the start of the reaction to form the calcium carbonate particles, i.e. not before the addition of the educts, preferably no earlier than 1 minute, preferably no earlier than 2 minutes, appropriately no earlier than 3 minutes, especially preferred no earlier than 4 minutes, especially no earlier than 5 minutes after mixing the educts. Further, the point in time of the addition should be selected so that the preferably surface-active substance is added shortly before the end of precipitation and as shortly as possible before the start of conversion of the preferably amorphous calcium carbonate to a crystalline modification, as in this way the yield and the purity of the "stabilized spherical amorphous calcium carbonate particles" can be maximized. If the preferably surface-active substance is added earlier, usually a bimodal product is obtained which comprises, apart from the desired stabilized spherical amorphous calcium carbonate particles, ultra-fine amorphous calcium carbonate particles as a side-product. If the preferably surface-active substance is added later, then the conversion of the desired "stabilized calcium carbonate particles" to crystalline modifications already starts.

For this reason, the preferably surface-active substance is preferably added at a pH value less than or equal to 11.5, preferably less than or equal to 11.3, especially less than or equal to 11.0. Especially favorable is an addition at a pH value in the range from 11.5 to 10.0, of preference in the range from 11.3 to 10.5, especially in the range from 11.0 to 10.8, each measured at the reaction temperature, preferably at 25° C.

The resulting stabilized preferably spherical amorphous calcium carbonate particles can be dehydrated and dried in a way known per se, e.g. by centrifugation. Washing with acetone and/or drying in a vacuum drying cabinet is no longer absolutely necessary.

By drying, it is possible to obtain "calcium carbonate particles having low structural water content" from the "stabilized calcium carbonate particles".

For the purposes of the present invention, the calcium carbonate particles obtained are preferably dried in such a way that they have the desired residual water content. A procedure in which the calcium carbonate particles are preferably first pre-dried at a temperature of up to 150° C. and then the calcium carbonate particles are preferably dried at a temperature in the range from greater than 150° C. to 250° C., preferably in the range from 170° C. to 230° C., particularly preferably in the range from 180° C. to 220° C., in particular in the range from 190° C. to 210° C., has proved to be particularly effective for this purpose. Drying is preferably carried out in a convection oven. It is advisable to dry the calcium carbonate particles for at least 3 hours, preferably at least 6 hours, in particular at least 20 hours.

With the scope of another particularly preferred embodiment of the present invention, the proportion of crystalline calcium carbonate, in particular of calcitic calcium carbonate, is greater than 10% by weight, preferably greater than 25% by weight, advantageously greater than 50% by weight, particularly preferred greater than 70% by weight, particularly preferred greater than 80% by weight, in particular greater than 90% by weight.

For establishing the amorphous and crystalline fractions, the X-ray diffraction with an internal standard, preferably aluminum oxide, in combination with a Rietveld refinement has particularly proven itself.

The basicity of the calcium carbonate particles is comparatively low. Their pH value, measured according to EN ISO 787-9, is preferably less than 11.5, preferably less than 11.0, and in particular less than 10.5.

The spherical calcium carbonate particles can be produced by carbonating an aqueous calcium hydroxide (Ca(OH)$_2$) suspension. For this purpose, $CO_2$ or a gas mixture containing $CO_2$ is conveniently fed into a calcium hydroxide suspension.

A procedure in which
a. an aqueous calcium hydroxide suspension is provided,
b. carbon dioxide or a gas mixture containing carbon dioxide is introduced into the suspension of step a. and
c. the forming calcium carbonate particles are separated,
  has especially proven itself, wherein 0.3 wt.-% to 0.7 wt.-%, preferably 0.4 wt.-% to 0.6 wt.-%, especially 0.45 wt.-% to 0.55 wt.-%, of at least one aminotrialkylene phosphonic acid is further added.

The concentration of the calcium hydroxide suspension is not subject to any particular restrictions. However, a concentration within the range from 1 g CaO/l to 100 g CaO/l, preferably within the range from 10 g CaO/l to 90 g CaO/l, especially within the range from 50 g CaO/l to 80 g CaO/l is especially favorable.

As aminotrialkylene phosphonic acid, preferably aminotrimethylene phosphonic acid, aminotriethylene phosphonic acid, aminotripropylene phosphonic acid and/or aminotributylene phosphonic acid, especially aminotrimethylene phosphonic acid is/are added.

The conversion of the reaction can be controlled by the quantity of $CO_2$ introduced. However, the introduction of carbon dioxide or the gas mixture containing carbon dioxide is preferably carried out until the reaction mixture has a pH value of less than 9, preferably less than 8, especially less than 7.5.

Furthermore, the carbon dioxide or the gas mixture containing carbon dioxide is expediently introduced at a gas flow rate within the range from 0.02 l $CO_2$/(h*g Ca(OH)$_2$) to 2.0 l $CO_2$/(h*g Ca(OH)$_2$), preferably within the range from 0.04 l $CO_2$/(h*g Ca(OH)$_2$) to 1.0 l $CO_2$/(h*g Ca(OH)$_2$), especially preferred within the range from 0.08 l $CO_2$/(h*g Ca(OH)$_2$) to 0.4 l $CO_2$/(h*g Ca(OH)$_2$), especially within the range from 0.12 l $CO_2$/(h*g Ca(OH)$_2$) to 0.2 l $CO_2$/(h*g Ca(OH)$_2$) into the calcium hydroxide suspension.

Incidentally, the conversion of the calcium hydroxide suspension with the carbon dioxide or the gas mixture containing carbon dioxide is carried out preferably at a temperature of less than 25° C., preferably less than 20° C., especially less than 15° C. On the other hand, the reaction temperature preferably is more than 0° C., preferably more than 5° C., especially more than 7° C.

The at least one aminotrialkylene phosphonic acid is expediently added in the course of the reaction, preferably after an abrupt drop of the conductance of the reaction mixture. Expediently, the at least one aminotrialkylene phosphonic acid is added as soon as the conductivity of the reaction mixture decreases by more than 0.5 mS/cm/min. The decrease of the conductivity of the reaction mixture preferably amounts to at least 0.25 mS/cm within 30 seconds, especially at least 0.5 mS/cm within 60 seconds. Within the scope of an especially preferred embodiment of the present invention, the at least one aminotrialkylene phosphonic acid is added at the end of precipitation of the basic calcium carbonate (BCC; $2CaCO_3$*$Ca(OH)_2$*$nH_2O$).

The calcium carbonate particles precipitate from the reaction mixture under the afore-mentioned conditions and can be separated and dried in a way known per se.

Within the scope of a preferred embodiment of the present invention, the composite powder used according to the invention in the implant contains, apart from calcium carbonate, further calcium salts, especially calcium phosphates, especially $Ca_3(PO_4)_2$, $CaHPO_4$, $Ca(H_2PO_4)_2$ and/or $Ca_5(PO_4)_3(OH)$. The weight ratio of calcium carbonate to calcium phosphate preferably is in the range from 99:1 to 1:99, especially in the range from 50:50 to 99:1.

Within the scope of a preferred embodiment of the present invention, the small particles comprise inhibiting calcium carbonate particles. In this context, "inhibiting calcium carbonate particles" denote calcium carbonate particles which as an additive in polymers decelerate, at the best completely suppress, the acid-catalyzed degradation of the polymer as compared to the same polymer without an additive.

Expediently, the small particles are obtainable by a process in which calcium carbonate particles are coated with a composition which contains, each related to its total weight, a mixture of at least 0.1 wt.-% of at least one calcium complexing agent and/or at least one conjugated base which is an alkali metal salt or calcium salt of a weak acid, together with at least 0.1 wt.-% of at least one weak acid.

The anions of the calcium complexing agent and of the conjugated base may be equal within the scope of this embodiment, although this is no mandatory requirement.

Sodium phosphates, i.e. sodium salts of phosphoric acids, especially sodium salts of orthophosphoric acid, metaphosphoric acid and polyphosphoric acid, have turned out to be especially advantageous as calcium complexing agents. Preferred sodium phosphates comprise sodium orthophosphates such as primary sodium dihydrogen phosphate $NaH_2PO_4$, secondary sodium dihydrogen phosphate $Na_2HPO_4$ and tertiary trisodium phosphate $Na_3PO_4$; sodium iso polyphosphates such as tetrasodium diphosphate (sodium pyrophosphate) $Na_4P_2O_7$, pentasodium triphosphate (sodium tripolyphosphate) $Na_5P_3O_{10}$; as well as higher-molecular sodium phosphates such as sodium metaphosphates and sodium polyphosphates such as fused or calcined phosphates, Graham's salt (approximate composition $Na_2O$*$P_2O_5$, occasionally also referred to as sodium hexametaphosphate), Kurrol's salt and Maddrell salt. Especially preferred, sodium hexametaphosphate is used according to the invention. The use of the afore-mentioned phosphates is especially advantageous in a composite powder for implants, as in this case the phosphates additionally promote the osseous structure.

Further suited calcium complexing agents include joint multidentate chelate-forming ligands, especially ethylene diamino tetra acetic acid (EDTA), triethylenetetramine, diethylenetriamine, o-phenanthroline, oxalic acid and mixtures thereof.

Weak acids especially suited for the purposes of the present invention have a pKa value, measured at 25° C., of more than 1.0, preferably more than 1.5, especially more than 2.0. At the same time, the pKa value of suited weak acids, measured at 25° C., is preferably less than 20.0, preferred less than 10.0, especially preferred less than 5.0, expediently less than 4.0, especially less than 3.0. Weak acids extraordinarily suited according to the invention comprise phosphoric acid, metaphosphoric acid, hexametaphosphoric acid, citric acid, boric acid, sulfurous acid, acetic acid and mixtures thereof. Phosphoric acid is used especially preferred as weak acid.

Conjugated bases preferred according to the invention include especially sodium salts or calcium salts of the afore-mentioned weak acids, with sodium hexametaphosphate being particularly preferred.

The inhibiting calcium carbonate particles can be prepared in a way known per se by coating calcium carbonate particles with a composition which comprises at least one calcium complexing agent and/or at least one conjugated base which is an alkali metal salt or calcium salt of a weak acid, together with at least one weak acid.

Expediently, an aqueous suspension of the calcium carbonate particles to be coated is provided which, based on its total weight, favorably has a content of calcium carbonate particles within the range from 1.0 wt.-% to 80.0 wt.-%, preferred within the range from 5.0 wt.-% to 50.0 wt.-%, especially within the range from 10.0 wt.-% to 25.0 wt.-%.

The coating process of the calcium carbonate particles is favorably carried out by adding said substances in pure form or in aqueous solution, wherein aqueous solutions of said components have turned out to be particularly advantageous according to the invention in order to obtain an as homogenous coating as possible of the calcium carbonate particles.

Further, it is especially favorable within the scope of the present invention to add the calcium complexing agent and/or the conjugated base, which is an alkali metal salt or calcium salt of a weak acid, before the weak acid.

The calcium complexing agent or the conjugated base is preferably used in a quantity ranging from 0.1 parts by weight to 25.0 parts by weight, preferably ranging from 0.5 parts by weight to 10.0 parts by weight, especially ranging from 1.0 parts by weight to 5.0 parts by weight, each related to 100 parts by weight of the calcium carbonate particles to be coated. Here, the quantity of the calcium complexing agent or of the conjugated base is expediently selected so that complete coating of the surface of the calcium carbonate particles with the calcium complexing agent of the conjugated base is obtained.

The weak acid is preferably used in a quantity ranging from 0.1 parts by weight to 30.0 parts by weight, preferably ranging from 0.5 parts by weight to 15.0 parts by weight, especially preferred ranging from 1.0 parts by weight to 10.0 parts by weight, especially ranging from 4.0 parts by weight to 8.0 parts by weight, each related to 100 parts by weight of the calcium carbonate particles to be coated.

The inhibiting calcium carbonate particles obtainable in this way are stable in a moderately acidic environment, wherein this capacity is due to a buffering action by the absorbed or converted calcium complexing agent or the conjugated base on the surface of the calcium carbonate particles and the weak acid in solution, wherein applying the calcium complexing agent and/or the conjugated base to the surface of the calcium carbonate particles in turn reduces the solubility of the surface of the calcium carbonate particles and thus stabilizes the calcium carbonate particles without the teaching of the present invention being intended to be bound to this theory.

Said composite powder is preferably obtainable by a method in which large particles are bonded to small particles, wherein
    the large particles have a mean particle diameter ranging from 0.1 µm to 10 mm, preferably ranging from 5 µm to 10 mm, especially preferred ranging from 10 µm to 10 mm, favorably ranging from 20 µm to 10 mm, advantageously ranging from 30 µm to 2.0 mm, in particular ranging from 60.0 µm to 500.0 µm,
    the mean particle diameter of the small particles preferably is no more than ⅕, preferably no more than ¹/₁₀, especially preferred no more than ¹/₂₀, especially no more than ¹/₁₀₀₀, of the mean particle diameter of the large particles.

The small particles are preferably arranged on the surface of the large particles and/or are non-homogeneously spread within the large particles. Especially for resorbable polymers and for UHMWPE excellent results are achieved, however, if the small particles are arranged on the surface of the large particles and preferably do not completely cover the latter.

A "non-homogeneous" distribution of the small particles or fragments thereof within the large particles in this case means a non-homogeneous (uniform) distribution of the small particles or fragments thereof within the large particles. Preferably, within the particles of the composite powder there is at least a first area comprising at least two, preferably at least three, preferred at least four, especially at least five small particles or fragments thereof and at least another area within the particles of the composite powder which, although taking the same volume and the same shape as the first area, comprises a different number of small particles.

Within the scope of a preferred embodiment of the present invention, the weight ratio of polymer, especially polyamide, to precipitated calcium carbonate within the particle interior is higher than the weight ratio of polymer, especially polyamide, to precipitated calcium carbonate in the outer area of the particles. Expediently, the weight ratio of polymer, especially polyamide, to precipitated calcium carbonate in the particle interior is higher than 50:50, preferred higher than 60:40, favorably higher than 70:30, especially preferred higher than 80:20, even more preferred higher than 90:10, particularly preferred higher than 95:5, especially higher than 99:1. Furthermore, the weight ratio of precipitated calcium carbonate to polymer, especially polyamide, in the outer area of the particles, preferably in the preferred outer area of the particles, is higher than 50:50, preferred higher than 60:40, favorably higher than 70:30, especially preferred higher than 80:20, even more preferred higher than 90:10, particularly preferred higher than 95:5, especially higher than 99:1.

Within the scope of another preferred embodiment of the present invention, the small particles are arranged on the surface of the large particles and preferably do not completely cover the large particles. Expediently, at least 0.1%, preferred at least 5.0%, especially 50.0%, of the surface of the large particles are not coated with the spherical calcium carbonate particles. This effect is preferably intensified by the gaps between individual calcium carbonate particles which are preferably formed and result in the formation of appropriate micro-channels for fluid substances, especially for a melt of the polymer of the large particles. Said structure is especially beneficial to applications of the composite powder in laser sintering methods, as in this way uniform and rapid melting of the polymer contained in the composite powder, preferably of the thermoplastic polymer, especially preferred of the resorbable polymer, especially of the lactic acid polymer, is ensured.

Within the framework of a particularly preferred embodiment of the present invention, the composite powder used in the implant according to the invention is characterized by a special particle size distribution. Firstly, the particles of the composite powder preferably have an average particle size $d_{50}$ in the range from 10 µm to less than 200 µm, preferably in the range from 20 µm to less than 200 µm, particularly preferably in the range from 20 µm to less than 150 µm, favorably in the range from 20 µm to less than 100 µm, particularly in the range from 35 µm to less than 70 µm.

Furthermore, the fine-grain fraction of the composite powder preferably is less than 50.0 vol %, preferred less than 45.0 vol %, especially preferred less than 40.0 vol %, even more preferred less than 20.0 vol %, favorably less than 15.0 vol %, expediently less than 10.0 vol %, especially less than 5.0 vol %. The fine-grain fraction denotes, according to the invention, the fraction of the smallest particle population in a bimodal or multimodal grain size distribution related to the total amount in the cumulative distribution curve. In unimodal (monodisperse) grain size distribution, the fine-grain fraction is defined as 0.0 vol %, according to the invention. In this context, all particles present in the product including non-bonded starting material, especially small particles within the meaning of the invention as well as pieces or fragments of the large and/or small particles in the sense of the invention are considered.

For composite powders having an average particle size $d_{50}$ ranging from more than 40 µm to less than 200 µm, the fine-grain fraction preferably is such that the fraction of particles within the product having a particle size of less than 20 µm is preferably less than 50.0 vol %, preferred less than 45.0 vol %, especially preferred less than 40.0 vol %, even more preferred less than 20.0 vol %, favorably less than 15.0 vol %, expediently less than 10.0 vol %, especially less than 5.0 vol %, wherein "particles" in this context comprise especially particles of the composite powder in accordance with the invention, small particles in accordance with the invention as well as pieces or fragments of the large and/or small particles in accordance with the invention, if they show said particle size.

For composite powders having a mean particle size $d_{50}$ ranging from 10 µm to 40 µm, the fine-grain fraction preferably is such that the fraction of particles within the product having a particle size of less than 5 µm is preferably less than 50.0 vol %, preferred less than 45.0 vol %, especially preferred less than 40.0 vol %, even more preferred less than 20.0 vol %, favorably less than 15.0 vol %, expediently less than 10.0 vol %, especially less than 5.0 vol %, wherein "particles" in this context comprise especially particles of the composite powder in accordance with the invention, small particles in accordance with the invention as well as pieces or fragments of the large and/or small particles in accordance with the invention, if they show said particle size.

Furthermore, the density of the fine-grain fraction preferably is less than 2.6 g/cm³, preferred less than 2.5 g/cm³, especially preferred less than 2.4 g/cm³, especially ranging from more than 1.2 g/cm³ to less than 2.4 g/cm³, said value being preferably determined by separating the fine-grain fraction by means of sieving and densitometry at the separated fraction.

Of preference, the particles of the composite powder have a particle size $d_{90}$ of less than 350 µm, preferably less than 300 µm, preferred less than 250 µm, especially preferred less than 200 µm, especially less than 150 µm. Further, the particle size $d_{90}$ preferably is more than 50 µm, preferred more than 75 µm, especially more than 100 µm.

Appropriately, the $d_{20}/d_{50}$ ratio is less than 100%, preferably less than 75%, preferred less than 65%, especially preferred less than 60%, especially less than 55%. Further, the $d_{20}/d_{50}$ ratio appropriately is more than 10%, preferably more than 20%, preferred more than 30%, especially preferred more than 40%, especially more than 50%.

The afore-mentioned variables $d_{20}$, $d_{50}$ and $d_{90}$ are defined as follows within the scope of the present invention:

$d_{20}$ denotes the particle size of the particle size distribution at which 20% of the particles have a particle size of less than the given value and 80% of the particles have a particle size of more than or equal to the given value.

$d_{50}$ denotes the mean particle size of the particle size distribution. 50% of the particles have a particle size of less than the given value and 50% of the particles have a particle size of more than or equal to the given value.

$d_{90}$ denotes the particle size of the particle size distribution at which 90% of the particles have a particle size of less than the given value and 10% of the particles have a particle size of more than or equal to the given value.

The particle size distribution according to the invention can be obtained in a way known per se by sizing the composite powder, i.e. by separating a disperse solid mixture into fractions. Preferably, sizing is carried out according to particle size or particle density. Especially advantageous are dry sieving, wet sieving and air jet sieving, especially air jet sieving, as well as flow sizing, especially by means of air separation.

Within the scope of an especially preferred embodiment of the present invention, the composite powder is sized in a first step to preferably remove the coarse fraction of more than 800 µm, preferred of more than 500 µm, especially of more than 250 µm. In this context, dry sieving via a coarse sieve which preferably has a size, i.e. the size of the holes, ranging from 250 µm to 800 µm, preferably ranging from 250 µm to 500 µm, especially of 250 mm, has proved its worth in particular.

In a further step, the composite powder is preferably sized to remove the fine-grain fraction of <20 µm at most. In this context, air jet sieving and air separation have turned out to be especially appropriate.

The mean diameters of the particles of the composite powder, the large particles and the small particles, the particle sizes $d_{20}$, $d_{50}$, $d_{90}$ as well as the afore-mentioned length dimensions are established according to the invention appropriately by way of microscopic images, where necessary by way of electron-microscopic images. For establishing the mean diameters of the large particles and the small particles as well as of the particles of the composite powder and for the particle sizes $d_{20}$, $d_{50}$ $d_{90}$, also sedimentation analyses are especially beneficial, with the use of a Sedigraph 5100 (Micromeritics GmbH) being especially useful in this case. For the particles of the composite powder, also particle size analyses by laser diffraction have especially proven themselves, in this context the use of a laser diffraction sensor HELOS/F by Sympatec GmbH being especially beneficial. The latter preferably comprises a RODOS dry dispersing system.

Incidentally, these indications as well as all other indications given in the present description refer to a temperature of 23° C., unless otherwise indicated.

The composite powder according to the invention is comparatively compact. Of preference, the share of portions inside the particles of the composite powder having a density of less than 0.5 g/cm³, especially less than 0.25 g/cm³, is less than 10.0%, preferred less than 5.0%, especially less than 1.0%, each related to the total volume of the composite powder.

The percentage by weight of the calcium carbonate particles, related to the total weight of the composite powder, preferably amounts to at least 0.1 wt.-%, preferred at least 1.0 wt.-%, especially preferred at least 5.0 wt.-%, and expediently is within the range from 5.0 wt.-% to 80.0 wt.-%, especially preferred within the range from 10.0 wt.-% to 60.0 wt.-%, favorably within the range from 20.0 wt.-% to 50.0 wt.-%. For spherical calcium carbonate particles which contain, related to the total quantity of spherical calcium carbonate particles, more than 15.0 wt.-% particles having a size of less than 20 µm and/or particles having a size of more than 250 µm, a total quantity of spherical calcium carbonate particles within the range from 35.0 wt.-% to 45.0 wt.-% has extraordinarily proven itself. For spherical calcium carbonate particles, which, related to the total quantity of spherical calcium carbonate particles, contain no more than 15.0 wt.-% of particles having a size of less than 20 µm and/or particles having a size of more than 250 µm, a total quantity of spherical calcium carbonate particles within the range from 20.0 wt.-% to 30.0 wt.-% has extraordinarily proven itself.

The percentage by weight of the polymer, preferably of the thermoplastic polymer, related to the total weight of the composite powder, amounts to preferably at least 0.1 wt.-%, preferred at least 1.0 wt.-%, especially preferred at least 5.0 wt.-%, and expediently ranges from 20.0 wt.-% to 95 wt.-%, preferred from 40.0 wt.-% to 90.0 wt.-%, favorably from 50.0 wt.-% to 80.0 wt.-%.

For a composite powder that contains spherical calcium carbonate particles which contain, related to the total quantity of spherical calcium carbonate particles, more than 20.0 wt.-% of particles having a size less than 20 µm and/or particles having a size of more than 250 µm, a total quantity of polymer ranging from 55.0 wt.-% to 65.0 wt.-% has extraordinarily proven itself. For a composite powder that contains spherical calcium carbonate particles which contain, related to the total quantity of spherical calcium carbonate particles, no more than 20.0 wt.-% of particles having a size of less than 20 µm and/or particles having a size of more than 250 µm, a total quantity of polymer ranging from 70.0 wt.-% to 80.0 wt.-% has particularly proven itself.

The composite powder excels, inter alia, by excellent bonding of the first material to the second material. The tight bonding of the first material to the second material preferably can be verified by mechanical loading of the composite powder, especially by shaking the composite powder with non-solvent for the polymer and spherical calcium carbonate, at 25° C., preferably according to the procedure described in Organikum, 17$^{th}$ Edition, VEB Deutscher Verlag der Wissenschaften, Berlin, 1988, Section 2.5.2.1 "Ausschütteln von Lösungen bzw. Suspensionen (Shaking of solutions and suspensions)", pp. 56-57. The shaking time preferably is at least one minute, preferably at least 5 minutes, especially 10 minutes, and preferably does not result in a substantial change of form, size and/or composition of the particles of the composite powder. According to the shaking test, especially preferred at least 60 wt.-%, preferably at least 70 wt.-%, preferred at least 80 wt.-%, especially preferred at least 90 wt.-%, favorably at least 95 wt.-%, especially at least 99 wt.-% of the particles of the composite powder are not changed with respect to their composition, their size and preferably their form. A non-solvent especially suited in this context is water, particularly for composite powder containing polyamide.

Furthermore, the particles of the composite powder used in the implant according to the invention usually exhibit a comparatively isotropic particulate form which is especially beneficial to applications of the composite powder in SLM methods. The usually almost spherical particulate form of the particles of the composite powder as a rule results in avoiding or at least reducing negative influences such as warpage or shrinkage. Consequently, usually also very advantageous melting and solidifying behavior of the composite powder can be observed.

In contrast to this, conventional powder particles obtained e.g. by cryogenic grinding have an irregular (amorphous) particulate form with sharp edges and corners. Powders of this type, however, are not advantageous for SLM methods due to their detrimental particulate form and, in addition, due to their comparatively broad particle size distribution and due to their comparatively high fine-grain fraction of particles of <20 µm.

The calcium carbonate particles, above all the precipitated calcium carbonate particles, help to specifically influence and control the properties of the polymer, especially of the thermoplastic polymer. In this way, the calcium carbonate particles, especially the precipitated calcium carbonate particles, enable proper buffering and pH stabilization of the polymer, especially of the thermoplastic polymer. Moreover, the biocompatibility of the polymer, especially of the thermoplastic polymer, is significantly improved by the calcium carbonate particles, especially by the precipitated calcium carbonate particles. In addition, when using the inhibiting calcium carbonate particles, significant suppression of the thermal degradation of the polymer, especially of the thermoplastic polymer, is observed.

Said composite powder used in the implant according to the invention may be prepared in a way known per se, for example by a single-step method, especially by precipitating or coating, preferably by coating with ground material. Further, even a procedure in which polymer particles are precipitated from a polymer solution which additionally contains small particles in accordance with the invention, preferably in suspended form, is especially suited.

However, a procedure in which polymer particles and spherical calcium carbonate particles are made to contact one another and are bonded to one another by the action of mechanical forces has especially proven itself. Appropriately, this is carried out in a suitable mixer or in a mill, especially in an impact mill, pin mill or ultra-rotor mill. The rotor speed preferably is more than 1 m/s, preferably more than 10 m/s, especially preferred more than 25 m/s, in particular in the range from 50 m/s to 100 m/s.

The temperature at which the composite powder is prepared can be freely selected in principle. However, especially advantageous are temperatures of higher than −200° C., preferably higher than −100° C., preferred higher than −50° C., especially preferred higher than −20° C., especially higher than 0° C. On the other hand, the temperature is advantageously less than 120° C., preferably less than 100° C., preferred less than 70° C., especially preferred less than 50° C., especially less than 40° C. Temperatures ranging from higher than 0° C. to less than 50° C., especially ranging from higher than 5° C. to less than 40° C. have turned out to be particularly useful.

Within the scope of an especially preferred embodiment of the present invention, the mixer or the mill, especially the impact mill, pin mill or ultra-rotor mill, is cooled during preparation of the composite powder according to the invention to dissipate the energy released. Preferably, cooling is effectuated by a coolant having a temperature of less than 25° C., preferred within the range from less than 25° C. to −60° C., especially preferred within the range from less than 20° C. to −40° C., appropriately within the range from less than 20° C. to −20° C., especially within the range from less than 15° C. to 0° C. Furthermore, the cooling preferably is dimensioned such that at the end of the mixing or grinding operation, preferably of the grinding operation, the temperature in the mixing or grinding chamber, especially in the grinding chamber, is less than 120° C., preferably less than 100° C., preferred less than 70° C., especially preferred less than 50° C., in particular less than 40° C.

According to an especially preferred embodiment of the present invention, this procedure results in the fact, especially for polyamides, that the spherical calcium carbonate particles penetrate the interior of the polymer particles and are preferably completely covered by the polymer so that they are not visible from outside. Such particles may be processed and used just as a polymer without the spherical calcium carbonate particles, but they exhibit the improved properties of said composite powder.

The composite powder is prepared in accordance with the procedure described in the patent application JP62083029 A. A first material (so-called mother particles) is coated on the surface with a second material consisting of smaller particles (so-called baby particles). For this purpose, preferably a surface modifying device ("hybridizer") is used comprising a high-speed rotor, a stator and a spherical vessel preferably comprising inner knives. The use of NARA hybridization systems preferably having an outer rotor diameter of 118 mm, especially of a hybridization system labeled NHS-0 or NHS-1 by NARA Machinery Co., Ltd., has especially proven itself in this context.

The mother particles and the baby particles are mixed, preferably very finely dispersed and introduced into the hybridizer. There, the mixture is preferably continued to be dispersed very finely and preferably repeatedly exposed to mechanical forces, especially impact forces, compressing forces, frictional forces and shear forces as well as the mutual interactions of the particles to uniformly embed the baby particles into the mother particles.

Preferred rotor speeds are within the range from 50 m/s to 100 m/s, related to the circumferential speed.

For further details concerning this method, JP62083029 A is referred to, the disclosure of which including the especially appropriate method variants is explicitly incorporated in the present application by reference.

Within the scope of another especially preferred variant, the composite powder is prepared in accordance with the procedure described in the patent application DE 42 44 254 A1. Accordingly, a method of preparing a composite powder by affixing a substance onto the surface of a thermoplastic material is especially favorable if the thermoplastic material has an average particle diameter from 100 μm to 10 mm and the substance has a lower particle diameter and better thermal resistance than the thermoplastic material, especially when the method comprises the following steps:

- at first heating the substance having the lower particle diameter and the better thermal resistance than the thermoplastic material to a temperature preferably no less than the softening point of the thermoplastic material during stirring in an apparatus which preferably includes a stirrer and a heater;
- adding the thermoplastic material to the apparatus; and
- affixing the substance having the better thermal resistance onto the surface of the thermoplastic material.

For further details concerning this method, reference is made to DE 42 44 254 A1, the disclosure of which including the especially appropriate method variants is explicitly incorporated in the present application by reference.

Alternatively, the composite powder is prepared in accordance with the procedure described in the patent application EP 0 922 488 A1 and/or in the U.S. Pat. No. 6,403,219 B1. Accordingly, a method of preparing a composite powder by affixing or bonding fine particles to the surface of a solid particle acting as a core by making use of impact and then allowing one or more crystals to grow on the core surface is especially advantageous.

For further details concerning this method, reference is made to patent application EP 0 922 488 A1 and/or U.S. Pat. No. 6,403,219 B1, the disclosures of which including the especially appropriate method variants are explicitly incorporated in the present application by reference.

By way of example, the composite powder may be subjected to fixation in accordance with the procedure described in patent application EP 0 523 372 A1. This procedure is useful especially for a composite powder which was obtained in accordance with the method described in the patent application JP62083029 A. The particles of the composite powder are preferably fixed by thermal plasma spraying, wherein preferably a reduced pressure plasma spraying device is used which preferably has a capacity of at least 30 kW, especially the apparatus described in EP 0 523 372 A1.

For further details concerning this method, reference is made to patent application EP 0 523 372 A1, the disclosure of which including the especially appropriate method variants is explicitly incorporated in the present application by reference.

The composite powder used in the implant according to the invention excels by an excellent property profile suggesting its use especially in laser sintering methods. Its excellent free-flowing property and its excellent flowability during laser sintering enable components of excellent surface quality and surface finish as well as of improved component density to be produced. At the same time, said composite powder exhibits very good shrinking behavior as well as excellent dimensional stability. Moreover, better thermal conductivity can be found outside the laser-treated area.

Moreover, said composite powder exhibits comparatively high isotropy which enables extremely uniform fusing of the composite powder. This behavior may be utilized in SLM processes for producing components of high quality, high component density, low porosity and a small number of defects.

Furthermore, the presence of the spherical calcium carbonate particles in the composite powder enables excellent pH stabilization (buffering) in later applications, especially in those polymers which contain acid groups or are adapted to release acids under certain conditions. These include, for example, polyvinylchloride and polylactic acid.

Moreover, said composite powder can possibly replace other, more expensive materials so as to achieve cost reduction of the final product.

The properties of the composite powder, especially its flowability, can also be controlled via the moisture of the composite powder and can be specifically adjusted as needed. On the one hand, the flowability of the composite powder basically increases with increasing moisture, thus facilitating processability of the composite powder. On the other hand, higher moisture of the composite powder may entail thermal degradation or hydrolysis of the polymer as well as process disruptions especially in the case of thermal processing of the composite powder primarily in the presence of impurities and/or in the presence of very fine particles.

Against this background, the moisture of said composite powder preferably is less than 2.5 wt.-%, preferred less than 1.5 wt.-%, especially preferred less than 1.0 wt.-%, even more preferred less than 0.9 wt.-%, favorably less than 0.8 wt.-%, expediently less than 0.6 wt.-%, particularly preferred less than 0.5 wt.-%, especially less than 0.25 wt.-%. On the other hand, the moisture of said composite powder preferably is more than 0.000 wt.-%, preferably more than 0.010 wt.-%, especially more than 0.025 wt.-%.

The use of the inhibiting calcium carbonate in this context enables even further improved thermal processability of the composite powder. The processing window (temperature window) is again significantly larger than by using conventional calcium carbonate, and thermal degradation or hydrolysis of a polymer is again significantly suppressed.

The desired moisture of the composite powder can be achieved by pre-drying, known per se, of the composite powder prior to processing, with drying being basically recommended in the production process. For stable process control in this context, drying up to a moisture content ranging from 0.01 wt.-% to 0.1 wt.-% has turned out to be especially favorable. Furthermore, the use of a microwave vacuum drier has especially proven itself.

The composite powder may be further processed in a comparatively simple manner because only one component (the composite powder) and no longer two components (spherical calcium carbonate particles and polymer) have to be processed. Problems of dispersion are not observed due to the tight bonding between the polymer and the spherical calcium carbonate particles.

Furthermore, the microstructure, the melting behavior and the flow behavior of the composite powder can be specifically controlled by the selection of the fractions and the size of the respective single components. These properties of the composite powder can be exploited, in turn, to specifically control the final structure of the resulting implants, especially the biocompatibility, the biodegradability and the mechanical properties thereof.

An addition of further processing aids, especially of specific solvents, usually is not required for processing the composite powder. This expands the possible fields of application of the composite powder especially in the pharmaceutical and food sectors.

The composite powder can be directly used as such. Due to its excellent property profile, the composite powder is especially suited, however, as an additive, especially preferred as a polymer additive, as an addition or starting material for compounding, for the production of implants, for applications in medical engineering and/or in microtechnology and/or for the production of foamed implants. Especially preferred applications in medical engineering include preferably resorbable implants. Especially expedient fields of application comprise injection-molded screws, pressed plates, especially melt-pressed plates, foamed implants as well as flowable powders for selective production methods, in the latter case the total particle size of the particles of the composite powder being preferably less than 3 mm and preferably more than 5.0 µm.

In the form of a polymer additive, the composite powder is preferably added to at least one polymer, especially to a thermoplastic polymer, as matrix polymer. In this case, the polymers which can also be used as a component of the composite powder are especially preferred. To avoid repetitions, reference is made to above explanations, especially as regards the preferred forms of the polymer. Extraordinarily preferred matrix polymers include polyvinylchloride (PVC), polyurethane (PU), silicone, polypropylene (PP), polyethylene (PE), especially UHMWPE, and polylactic acid (PLA).

The matrix polymer and the polymer of the composite powder can preferably be mixed at the temperature of use; with preference, they are chemically identical.

Especially preferred compositions contain 40.0 wt.-% to 99.9 wt.-%, of at least one matrix polymer and 0.1 wt.-% to 50.0 wt.-% of at least one such composite powder.

The production of the composition may be carried out in a manner known per se by mixing the components.

The composition then can be further processed in the usual way, especially granulated, ground, extruded, injection-molded, foamed or else used in 3D printing methods.

Furthermore, the composite powder can be further processed and/or used directly, i.e. without the addition of any further polymers.

The advantages of the composite powder can be observed especially when granulating, extruding, injection-molding, melt-pressing, foaming and/or 3D printing the composite powder.

Polymer foams are preferably produced by generating or introducing a gaseous phase in/into a composition comprising the composite powder and at least one matrix polymer, where necessary. The aim here is to distribute the gas as uniformly as possible within the composition so as to obtain a uniform and homogeneous foam structure. The gas may be introduced in various ways.

Of preference, the gaseous phase is generated by adding a blowing agent. Blowing agents are substances which release gases by chemical reactions (chemical blowing agents) or by phase transition (physical blowing agents). In foam extrusion or in foam injection molding, the chemical blowing agent is admixed to the composition in the form of a master batch, and a physical blowing agent is injected under pressure directly into the melt of the composition. The injection is referred to as direct gassing and is used especially in processing thermoplastic polymers.

Moreover, said composite powder per se is suited especially for producing implants adapted to replace conventional implants made from metal in the case of bone fractures. The implants serve for fixing the bones until the fracture has healed up. While implants of metal are normally retained in the body or have to be removed by further operation, the implants obtainable from the composite powder according to the invention act as temporary aids. They expediently comprise polymers which the body itself can degrade and substances which provide calcium and preferably valuable phosphorus substances for osteogenesis. The advantages resulting for the patient are obvious: no further operation for removing the implant and accelerated regeneration of the bones.

According to an especially preferred variant of the present invention, said composite powder is used for producing implants by selective laser sintering. Expediently, particles of the composite powder according to the invention tightly packed next to one another to form a powder bed are locally slightly surface-fused or melted (the polymer only) with the aid of a laser-scanner unit, a directly deflected electron beam or an infrared heating having a mask depicting the geometry. They solidify by cooling down due to heat conduction and thus combine to form a solid layer. The powder granules that are not surface-fused remain as supporting material within the component and are preferably removed after completion of the building process. By repeated coating with powder, analogously to the first layer further layers can be solidified and bonded to the first layer.

Types of lasers especially suited for laser sintering methods are all those which cause the polymer of the composite powder according to the invention to sinter, to melt or to crosslink, especially $CO_2$ lasers (10 µm), ND-YAG lasers (1,060 nm), He—Ne lasers (633 nm) or dye lasers (350-1, 000 nm). Preferably, a $CO_2$ laser is used.

The energy density in the filling during radiation preferably ranges from 0.1 $J/mm^3$ to 10 $J/mm^3$.

The active diameter of the laser beam preferably ranges from 0.01 nm to 0.5 nm, preferably 0.1 nm to 0.5 nm, depending on the application.

Of preference, pulsed lasers are used, wherein a high pulse frequency, especially from 1 kHz to 100 kHz, has turned out to be particularly suited.

The preferred procedure can be described as follows:

The laser beam is incident on the uppermost layer of the filling of said material to be used according to the invention and, in so doing, sinters the material at a predetermined layer thickness. Said layer thickness may be from 0.01 mm to 1 mm, preferably from 0.05 mm to 0.5 mm. In this way, the first layer of the desired implant is produced. Subsequently, the working space is lowered by an amount which is less than the thickness of the sintered layer. The working space is filled up to the original height with additional polymer material. By repeated radiation with the laser, the second layer of the implant is sintered and bonded to the preceding layer. By repeating the operation, the further layers are produced until the implant is completed.

The exposure rate during laser scanning preferably ranges from 1 mm/s to 1,000 mm/s. Typically, a rate of about 100 mm/s is applied.

In the present case, for surface-fusing or melting the polymer it has especially proven itself to heat to a temperature within the range from 60° C. to 250° C., preferably within the range from 100° C. to 230° C., especially within the range from 150° C. to 200° C.

The subject matter of the present invention further includes implants which are obtainable by selective laser sintering of a composition comprising said composite powder, wherein implants for applications in the field of neuro, oral, maxillary, facial, ear, nose and throat surgery as well as hand, foot, thorax, costal and shoulder surgery are especially preferred.

The percentage of said composite powder in the composition is preferably at least 50.0 wt.-%, preferred at least 75.0 wt.-%, especially preferred at least 90 wt.-%, in particular at least 99.0 wt.-%. Within the scope of a particular embodiment of the present invention, the composition contains exclusively the composite powder according to the invention.

The implants according to the invention appropriately excel by the following properties:
  excellent surface quality,
  excellent surface finish,
  excellent component density, preferably more than 95%, especially more than 97%,
  excellent shrinking behavior,
  excellent dimensional stability,
  very few defects,
  very low porosity,
  very low content of degradation products,
  excellent three-point flexural strength, preferably more than 60 MPa, especially preferred more than 65 MPa, especially more than 70 MPa,
  excellent elasticity modulus, preferably of 3420 N/mm$^2$, especially preferred of more than 3750 N/mm$^2$, favorably of more than 4000 N/mm$^2$, especially of more than 4500 N/mm$^2$,
  excellent pH stability,
  excellent biocompatibility,
  excellent osteo-conduction,
  excellent resorbing capacity,
  excellent biodegradability.

The subject-matter of the invention also includes the spherical calcium carbonate particles, which can be advantageously used to produce the composite particles in accordance with the invention, and their use.

Thus, the present invention also refers to spherical calcium carbonate particles in implants obtainable by a process in which
  a. a calcium hydroxide suspension is provided,
  b. carbon dioxide or a gas mixture containing carbon dioxide is introduced into the suspension from step a. and
  c. the calcium carbonate particles formed are separated,
wherein 0.3% by weight to 0.7% by weight of at least one aminotrialkylene phosphonic acid is further added.

With regard to the preferred design of these spherical calcium carbonate particles and the preferred methods for their production, the above explanations apply analogously.

Preferred applications for said spherical calcium carbonate particles include their use as additives for paper, plastics, paints and/or coatings, elastomers, adhesives and sealants, in construction chemicals, dry mortars and medical technology, especially as additives in resorbable polymers.

In particular those compositions which comprise, based in each case on the total weight of the composition,
  a) at least 0.1 wt. %, preferably at least 0.2 wt. %, in particular at least 0.5 wt. % to 50.0 wt. %, of at least one spherical calcium carbonate, and
  b) at least 0.1% by weight, preferably at least 0.2% by weight, in particular at least 0.5% by weight to 50.0% by weight, of at least one polymer, preferably at least one thermoplastic polymer, in particular preferably at least one resorbable polymer, in particular at least one poly-D-, poly-L- and/or poly-D-L-lactic acid, the advantages and effects mentioned in this application can be observed analogously, in particular as regards the improvement of the mechanical properties and the acid stability of the composition. With regard to the preferred choice of polymer, the above explanations apply analogously.

In the following, the present invention will be illustrated in more detail by several examples and comparison examples, without any limitation of the idea of the invention.

Materials used:
  granulate 1 (poly(L-lactide); inherent viscosity: 0.8-1.2 dl/g (0.1% in chloroform, 25° C.); Tg: 60-65° C.; Tm: 180-185° C.)
  granulate 2 (poly(L-lactide); inherent viscosity 1.5-2.0 dl/g (0.1% in chloroform; 25° C.)); Tg: 60-65° C.;
  granulate 3 (poly(D,L-lactide); inherent viscosity 1.8-2.2 dl/g (0.1% in chloroform; 25° C.)); Tg: 55-60° C.; amorphous polymer without melting point.

The mean particle diameter of each of the polylactide granulates 1 to 3 was within the range from 1 to 6 mm.

Within the scope of the present examples, the following variables were established as follows:
  $CaCO_3$ content: The $CaCO_3$ content was established by means of thermogravimetry by an STA 6000 by Perkin Elmer under nitrogen within the range from 40° C. to 1000° C. at a heating rate of 20° C./min. The weight loss was determined between about 550° C. and 1000° C. and therefrom the $CaCO_3$ content was calculated in percent through the factor 2.274 (molar mass ratio $CaCO_3:CO_2$).
  β-tricalcium phosphate content (β-TCP content): The β-TCP content was established by means of thermogravimetry by an STA 6000 by Perkin Elmer under nitrogen within the range from 40° C. to 1000° C. at a heating rate of 20° C./min. The weight percentage retained at 1000° C. corresponds to the β-TCP content in percent.
  $T_P$: The peak temperature $T_P$ was established by means of thermogravimetry by an STA 6000 by Perkin Elmer under nitrogen within the range from 40° C. to 1000° C. at a heating rate of 20° C./min. The peak temperature of the first derivation of the mass loss curve corresponds to the temperature with the maximum mass loss during polymer degradation.
  $d_{20}$, $d_{50}$, $d_{90}$: The grain size distribution of the calcium carbonate-containing composite powder was determined by laser diffraction (HELOS measuring range R5 with RODOS dispersing system by Sympatec). The grain size distribution was determined for the calcium carbonate powder by the Sedigraph 5100 with Master Tech 51 by Micromeretics. The dispersing solution used was 0.1% sodium polyphosphate solution (NPP).
  Fraction <20 μm: determination analogously to $d_{50}$. Evaluation of the fraction <20 μm.
  Moisture: The water content of the calcium carbonate containing composite powder was determined by a Karl Fischer Coulometer C30 by Mettler Toledo at 150° C. The water content of the calcium carbonate powders was determined by the halogen-moisture analyzer HB43 by Mettler at 130° C. (weighted sample: 6.4-8.6 g of powder; measurement time: 8 minutes).
  Inherent viscosity: The inherent viscosity (dl/g) was determined with a viscometer by Ubbelohde capillary 0c in chloroform at 25° C. and 0.1% polymer concentration.

Flowability: The flowability of the samples was judged by an electromotive film applicator by Erichsen. A 200 μm and, resp., 500 μm doctor blade was used for this purpose. The application rate to the foil type 255 (Leneta) was 12.5 mm/s. Rating as follows: 1=excellent, 2=good, 3=satisfactory; 4=sufficient; 5=poor Determination of the Mechanical Properties at Injection-Molded Specimens:

Three-point flexural strength and E modulus were determined by means of Texture Analyser TA.XTplus (Stable Micro Systems, Godalming (UK)). The capacity of the load cell used was 50 kg. Exponent 6.1.9.0 software was used. The details of measurement are shown in the following Table 1:

TABLE 1

| Load means: | Three-point load under DIN EN 843-1 |
| --- | --- |
| | Diameter of support/load rolls: 5.0 mm |
| Measurement: | In accordance with DIN EN ISO 178 |
| | Support distance: 45.0 mm |
| | Testing speed: 0.02 mm/s |
| | Preliminary speed: 0.03 mm/s |
| | Force/path recording |
| Specimens: | Dimensions about 3 mm × 10 mm × 50 mm |
| | After production (injection molding) storing until measurement in desiccator at room temperature n ≥5 |

Specimens were produced by HAAKE MiniLab II extruder and, resp., injection molding by HAAKE MiniJet II. The process conditions for specimen production are listed in the following Table 2:

TABLE 2

| Composite | Temperature Extruder [° C.] | Temperature injection-molding [° C.] | Temperature injection mold [° C.] | Pressure injection molding [bar] | Time injection molding [s] |
| --- | --- | --- | --- | --- | --- |
| Example 3 | 180 | 180 | 80 | 700 | 10 |
| Example 4 | 180 | 180 | 70 | 700 | 10 |
| Example 5 | 185 | 185 | 80 | 700 | 10 |
| Example 6 | 195 | 195 | 80 | 700 | 10 |
| Example 7 | 175 | 175 | 72 | 700 | 10 |
| Comparison 1 | 175 | 175 | 70 | 700 | 10 |

Cytotoxicity Test

The cytotoxicity test (FDA/GelRed) was carried out as follows:

The reference and, resp., negative control used was Tissue Culture Polystyrene (TCPS). Four replicates were used for each sample and four TCPS (4×) were used for control.

Test Procedure:
1. The non-sterile samples were made available in a 24 well microtiter plate. In the latter, the samples and the TCPS plates were sterilized with 70% ethanol (undenatured), then for 2×30 min rinsed with 1×PBS (phosphate-buffered saline solution) and after that equilibrated with sterile a medium. Then, the samples were inoculated with MC3T3-E1 cells with an inoculation coverage of 25,000 cells/cm$^2$ (50,000 cells/ml).

A partial medium exchange (1:2) took place on day 2.
2. After 1 and 4 days in cell culture, the cytotoxicity was determined.
3. Vital staining was carried out on day 1 and 4 according to standard protocol by means of combined staining of FDA and GelRed.
4. The microscopic images were produced at an Observer Z1m/LSM 700.
   Lens: EC Plan-Neofluar 10×;
   Images taken by camera AxioCam HRc:
   Excitation of green fluorescence: LED Colibri 470; filter set FS10 (AF488)
   Excitation of red fluorescence: LED Colibri 530; filter set FS14 (AF546)
   Images scanned in the laser scan mode:
   Track 1: laser: 488 nm, DBS 560 nm, PMT1: 488-560 nm,
   Track 2: laser 555 nm, DBS 565 nm, PMT2: 565-800 nm
5. Evaluation was made according to the following cytotoxicity scale:
   Acceptance: the material is not cytotoxic (max. 5% of dead cells)
   Slight inhibition: the material is slightly toxic (5%-20% of dead cells)
   Significant inhibition: the material is moderately toxic (20%-50% of dead cells)
   Toxicity: the material is highly cytotoxic (>50%-100% dead cells)
6. The cell numbers relate to the image detail taken or scanned.

The results are listed in Table 3.

Electron Microscope (SEM)

The SEM images were taken by a high-voltage electron microscope (Zeiss, DSM 962) at 15 kV. The samples were sprayed with a gold-palladium layer.

EXAMPLE 1

A $CO_2$ gas mixture containing 20% of $CO_2$ and 80% of $N_2$ was introduced into 4 l of calcium hydroxide suspension having a concentration of 75 g/l CaO at an initial temperature of 10° C. The gas flow was 300 l/h. The reaction mixture was stirred at 350 rpm and the reaction heat was dissipated during reaction. Upon abrupt drop of the conductance (drop of more than 0.5 mS/cm/min and decrease of the conductance by more than 0.25 mS/cm within 30 seconds), 0.7% of amino tri(methylene phosphonic acid), based on CaO (as theoretical reference value), is added to the suspension. The conversion to the spherical calcium carbonate particles was completed when the reaction mixture was carbonated quantitatively in relation to the spherical calcium carbonate particles, wherein the reaction mixture then showed a pH value between 7 and 9. In the present case, the reaction was completed after about 2 h and the reaction mixture had a pH value of 7 at the reaction end.

The resulting spherical calcium carbonate particles were separated and dried in a conventional way. They showed a mean particle diameter of 12 μm. A typical SEM image is shown in FIG. 1.

EXAMPLE 2

500 ml of VE (demineralized) water were provided in a 1000 ml beaker. 125 g of spherical calcium carbonate particles according to Example 1 were added under stirring and the resulting mixture was stirred for 5 min 37.5 g of a 10% sodium metaphosphate $(NaPO_3)_n$ solution were slowly added and the resulting mixture was stirred for 10 min 75.0 g of 10% phosphoric acid were slowly added and the resulting mixture was stirred for 20 h. The precipitation is separated and dried in the drying cabinet over night at 130° C. The resulting spherical calcium carbonate particles equally had a mean particle diameter of 12 μm.

Figure 2:

An SEM image of the spherical calcium carbonate particles is shown in FIG. 2. On the surface of the spherical calcium carbonate particles, a thin phosphate layer is visible.

EXAMPLE 3

A composite powder of spherical calcium carbonate particles and a polylactide (PLLA) was prepared in accordance with the method described in JP 62083029 A using the NHS-1 apparatus. It was cooled with water at 12° C. A polylactide granulate 1 was used as mother particles and the spherical calcium carbonate particles of Example 1 were used as the baby particles (filler).

39.5 g of polylactide granulate were mixed with 26.3 g $CaCO_3$ powder and filled at 6.400 rpm. The rotor speed of the unit was set to 6.400 rpm (80 m/s) and the metered materials were processed for 10 min. The maximum temperature reached in the grinding chamber of NHS-1 was 35° C. A total of 7 repetitions were carried out with equal material quantities and machine settings. A total amount of 449 g of composite powder was obtained. The composite powder obtained was manually dry-sieved through a 250 µm sieve. The sieve residue (fraction >250 µm) was 0.4%.

Figure 3A:

An SEM image of the composite powder obtained is shown in FIG. 3a.

EXAMPLES 4 TO 7

Further composite powders were prepared analogously to Example 3, wherein in Example 5 cooling took place at about 20° C. In each case 30 g of polylactide granulate were mixed with 20 g of $CaCO_3$ powder. The maximum temperature reached within the grinding chamber of NHS-1 was 33° C. for Example 4, 58° C. for Example 5, 35° C. for Example 6 and 35° C. for Example 7. The products were sieved to remove the course fraction >250 µm where possible (manual dry sieving through 250 µm sieve). In the Examples 4, 6 and 7, additionally the fraction <20 µm was classified by flow where possible (by means of air separation) or by sieving (by means of air jet sieving machine). The materials used, the implementation of the preparation with or without sieving/air separation as well as the properties of the composite powders obtained are listed in the following Table 3.

Figure 3B:
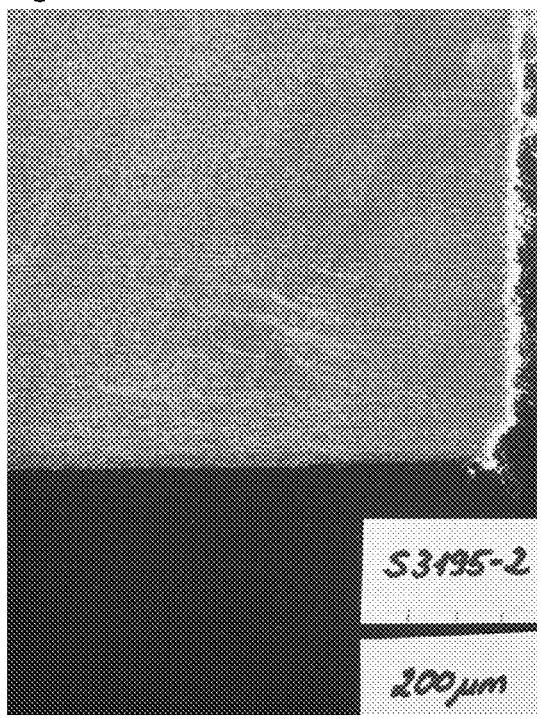
Figure 3C:

FIG. 3a, FIG. 3b and FIG. 3c illustrate an SEM image of Example 3 and images of plural doctor blade applications (12.5 mm/s) of Example 3 (FIG. 3b: 200 µm doctor blade; FIG. 3c: 500 µm doctor blade).

The SEM image of the composite powder obtained is shown in FIG. 3a. In contrast to the edgy irregular particulate form which is typical of the cryogenically ground powders, the particles of the composite powder obtained show a round particulate form and also high sphericity, with both attributes being very advantageous to SLM methods. The PLLA surface is sparsely occupied with spherical calcium carbonate particles and fragments thereof. The sample has a wide particle size distribution having increased fine-grain fraction.

The powder is flowable to a restricted extent (FIGS. 3b and 3c). A powder heap is pushed along in front of the doctor blade. The restricted flow behavior, probably caused by a higher fraction of fine particles, causes only very thin layers to be formed by both doctor blades.

Figure 4A:
Figure 4B:
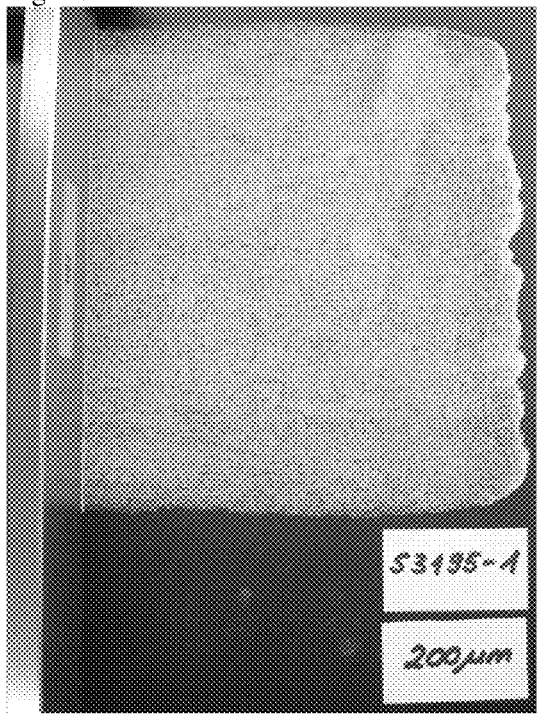
Figure 4C:
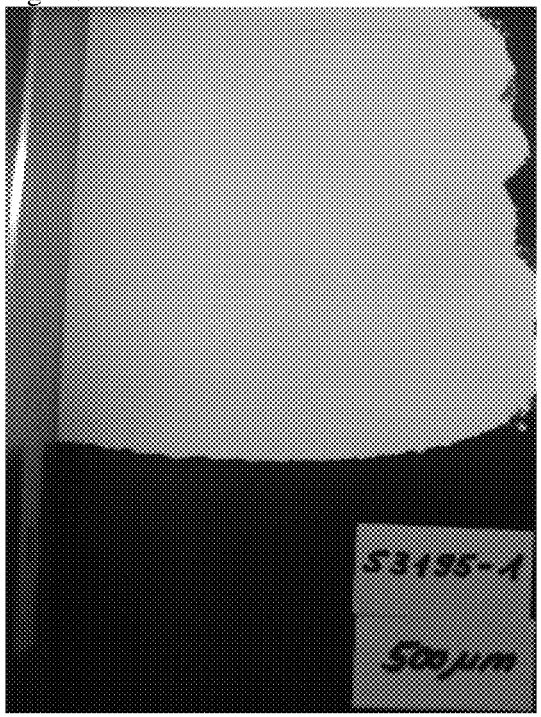

FIG. 4a, FIG. 4b and FIG. 4c illustrate an SEM image of Example 4 as well as images of plural doctor blade applications (12.5 mm/s) of Example 4 (FIG. 4b: 200 µm doctor blade; FIG. 4c: 500 µm doctor blade).

The SEM image of the composite powder obtained is shown in FIG. 4a. In contrast to the edgy irregular particulate form which is typical of the cryogenically ground powders, the particles of the composite powder obtained show a round particulate form and also high sphericity, with both attributes being very advantageous to SLM methods. The PLLA surface is sparsely occupied with spherical calcium carbonate particles and fragments thereof. The sample exhibits a considerably smaller particle size distribution having a small fine-grain fraction.

The powder has a very good flowability and can be applied very well by doctor blades (FIGS. 4b and 4c). The thin layers (200 µm), too, can be applied by doctor blades and are largely free from doctor streaks (tracking grooves). The powder layer applied with a doctor blade with 500 µm is homogeneous, densely packed, smooth and free from doctor streaks.

Figure 5A:
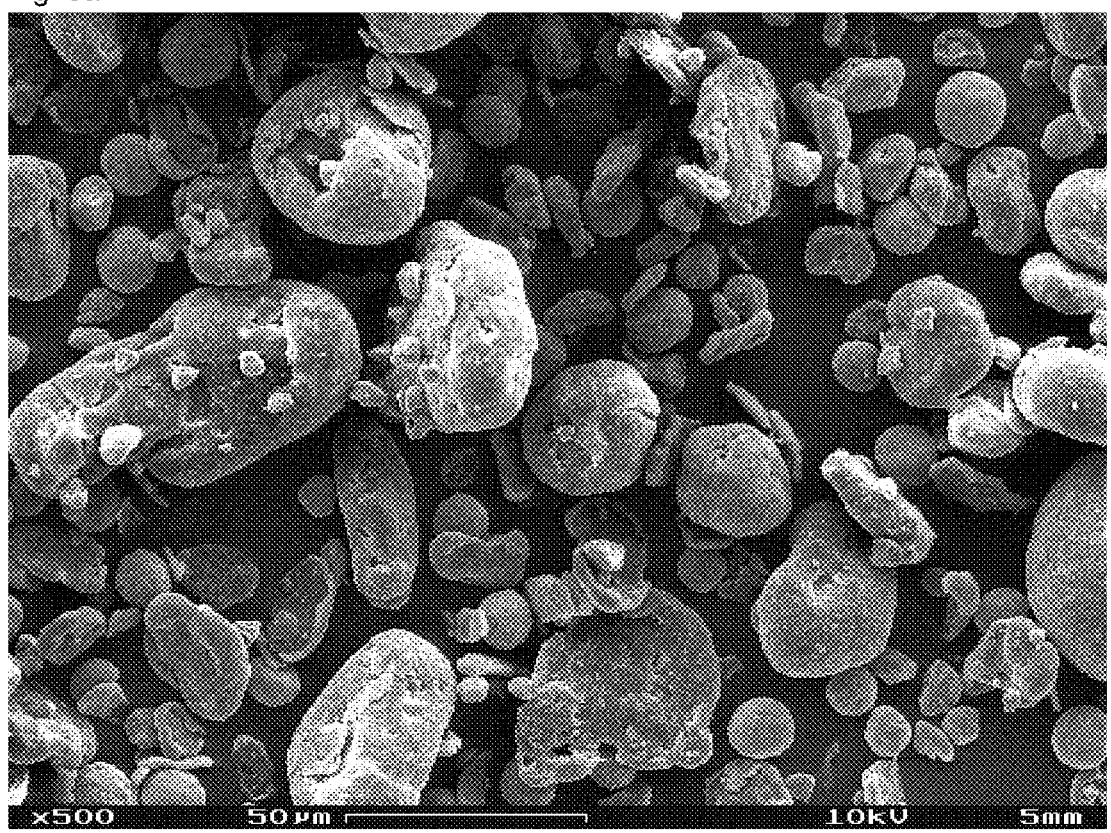
Figure 5B:
Figure 5C:
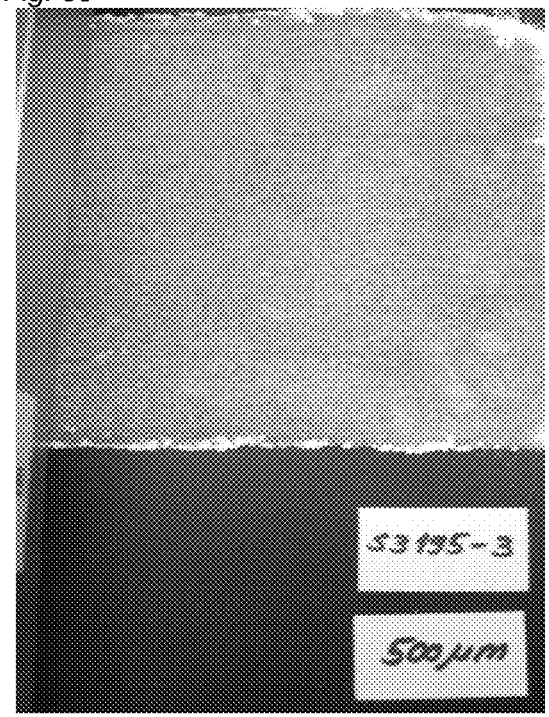

FIG. 5a, FIG. 5b and FIG. 5c illustrate an SEM image of Example 5 as well as images of several applications (12.5 mm/s) of Example 5 (FIG. 5b: 200 µm doctor blade; FIG. 5c: 500 µm doctor blade). The powder is flowable to a restricted extent. A powder heap is pushed along by the doctor blade. Due to the restricted flow behavior, probably caused by a higher fraction of fine particles, only very thin layers are formed by both doctor blades.

Figure 6A:
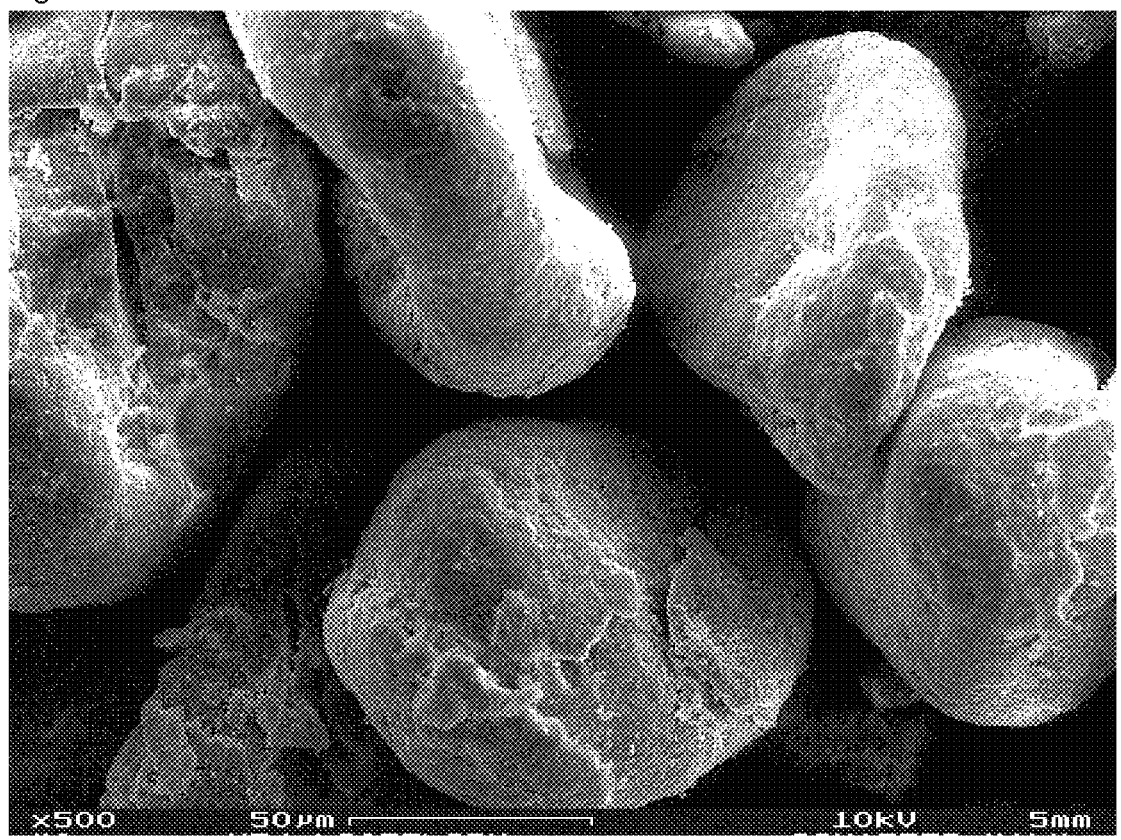
Figure 6B:
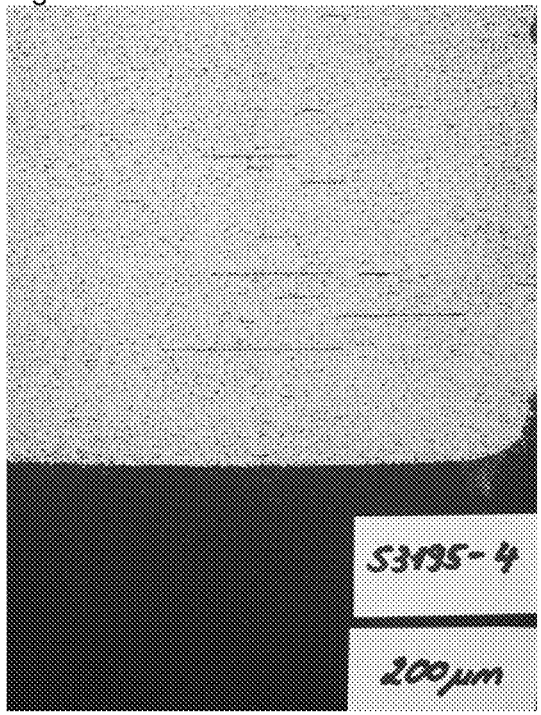
Figure 6C:

FIG. 6a, FIG. 6b and FIG. 6c illustrate an SEM image of Example 6 as well as images of plural applications (12.5 mm/s) of Example 6 (FIG. 6b: 200 µm doctor blade; FIG. 6c: 500 µm doctor blade). The powder has a good flowability and can be applied well by doctor blades. The thin layers (200 µm), too, can be applied. Individual doctor streaks caused by probably too coarse powder particles are visible. The powder layer applied with 500 µm is not quite densely packed but is free from doctor streaks.

Figure 7A:
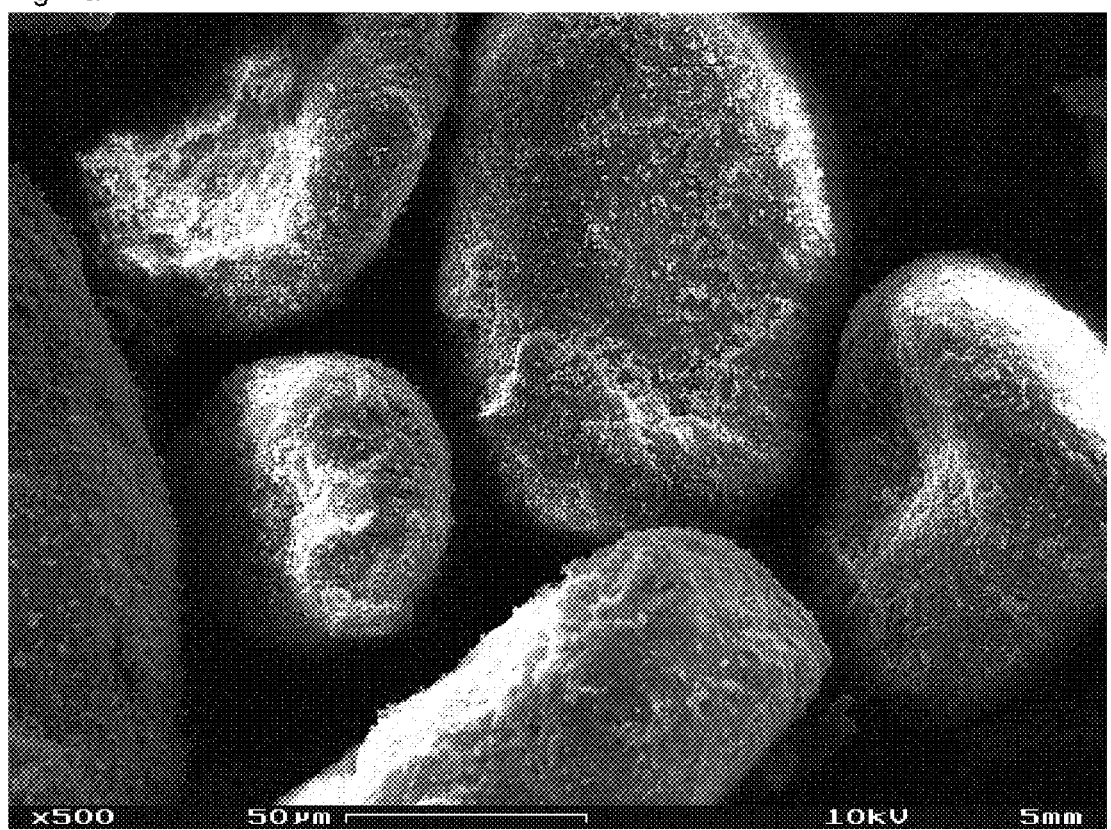
Figure 7B:
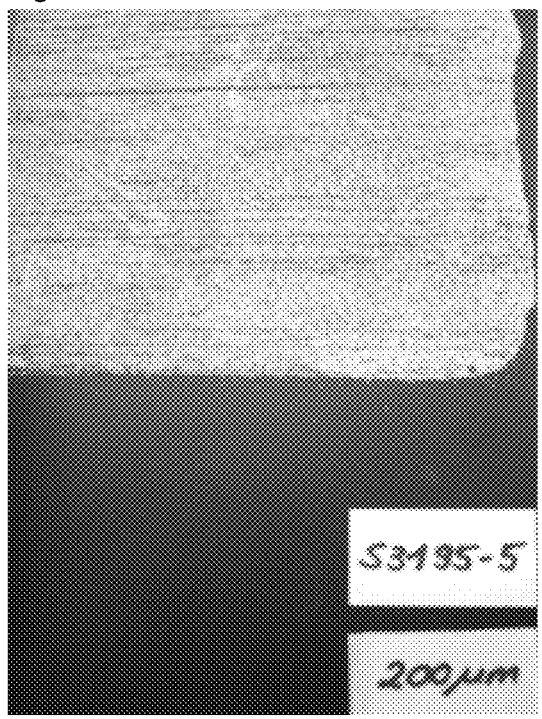
Figure 7C:
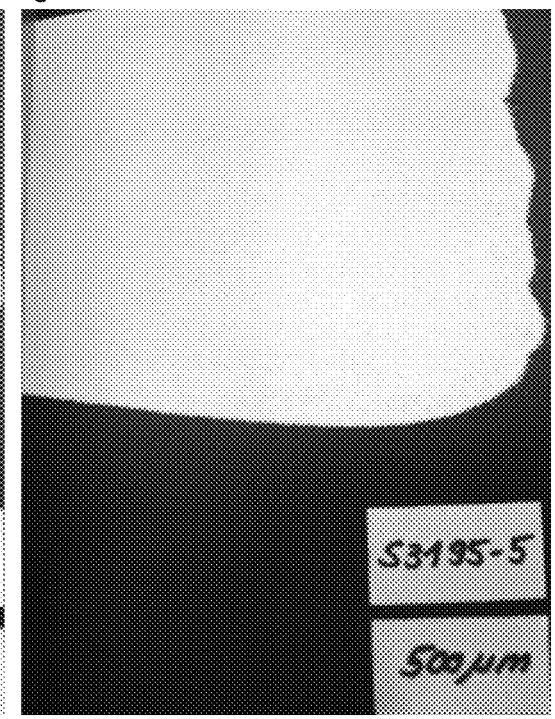

FIG. 7a, FIG. 7b and FIG. 7c illustrate an SEM image of Example 7 as well as images of plural applications (12.5 mm/s) of Example 7 (FIG. 7b: 200 µm doctor blade; FIG. 7c: 500 µm doctor blade). The powder is properly flowable and applicable. The thin layers (200 µm), too, can be applied. They are not homogeneous and are increasingly interspersed with doctor streaks. A somewhat restricted flow behavior is probably caused by too coarse powder particles. The powder layer applied with 500 µm is homogeneous and free from doctor streaks.

Comparison 1

Microstructured composite particles of spherical calcium carbonate particles of Example 1 and an amorphous polylactide (PDLLA) were prepared in accordance with the method described in JP 62083029 A using the NHS-1 apparatus. It was cooled with water at 12° C. A polylactide granulate 3 was used as mother particles and the spherical calcium carbonate particles of Example 1 were used as the baby particles.

39.5 g of polylactide granulate were mixed with 10.5 g of $CaCO_3$ powder and filled at 8,000 rpm. The rotor speed of the unit was set to 8,000 rpm (100 m/s) and the metered materials were processed for 1.5 min. The maximum temperature reached within the grinding chamber of the NHS-1 was 71° C. A total of 49 repetitions was carried out with equal material quantities and machine settings. A total amount of 2376 g of structured composite particles were obtained. The obtained structured composite particles were manually dry-sieved through an 800 µm sieve for measuring the particle size distribution. The sieve residue (fraction > 800 µm) amounted to 47%.

The properties of the microstructured composite particles obtained are listed in the following Table 3.

Figure 8A:
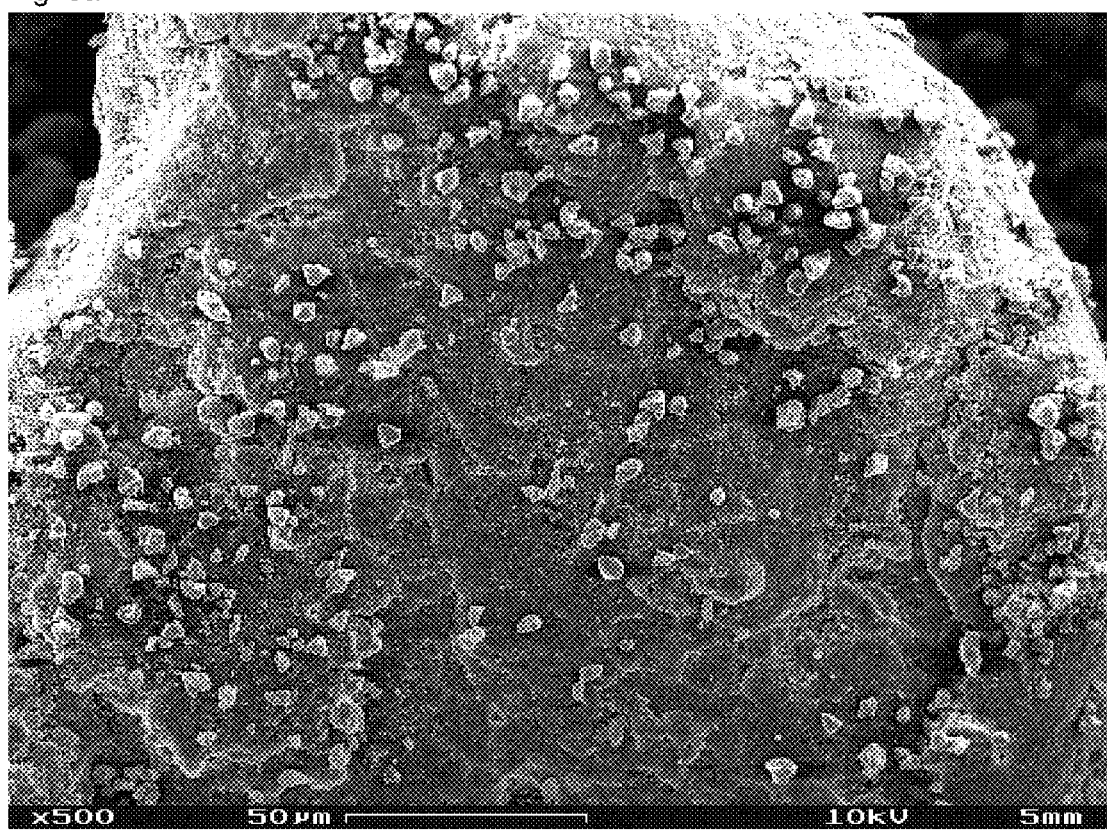
Figure 8B:
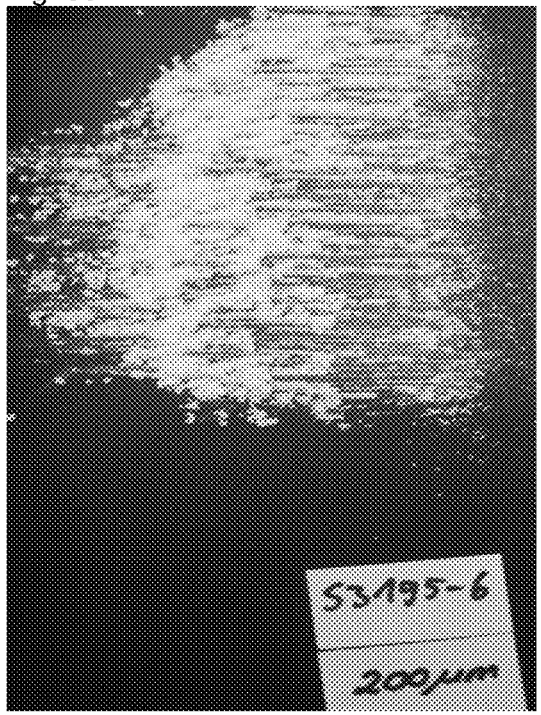
Figure 8C:
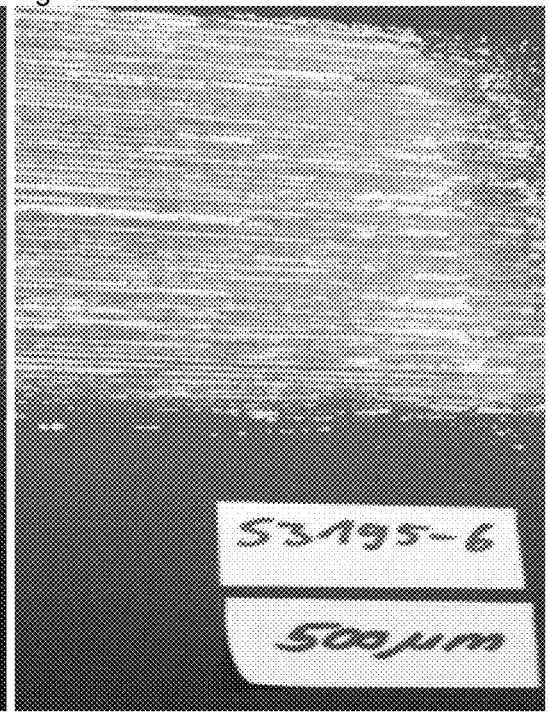

FIG. 8a, FIG. 8b and FIG. 8c illustrate an SEM image of Comparison 1 as well as images of plural applications (12.5 mm/s) of Comparison 1 (FIG. 8b: 200 μm doctor blade; FIG. 8c: 500 μm doctor blade). The powder is poorly flowable and cannot be applied to form layer thicknesses of 200 and, resp., 500 μm. The too coarse irregular particles get jammed during application by doctor blade. Non-homogeneous layers having very frequent and distinct doctor streaks are formed.

The SEM analysis shows that the surfaces of the structured composite particles are sparsely occupied with spherical calcium carbonate particles and the fragments thereof. As compared to the Examples 3 to 7, the particles show a more irregular particle geometry.

EXAMPLE 8

Figure 9A:
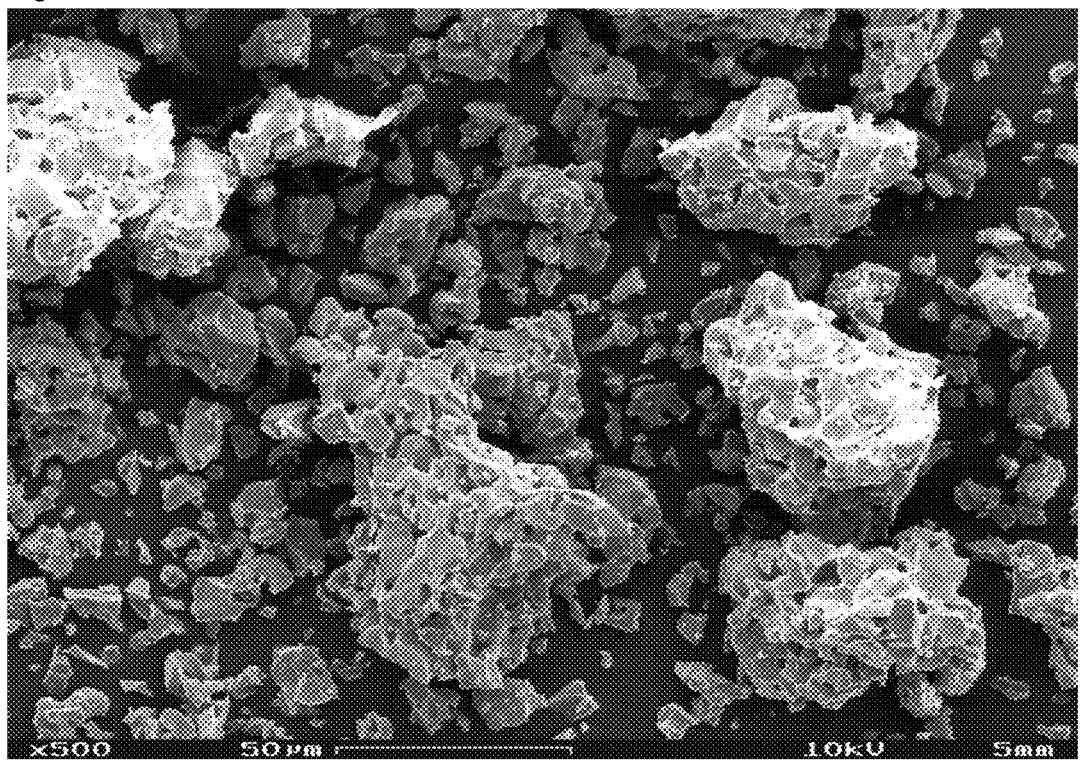
Figure 9B:
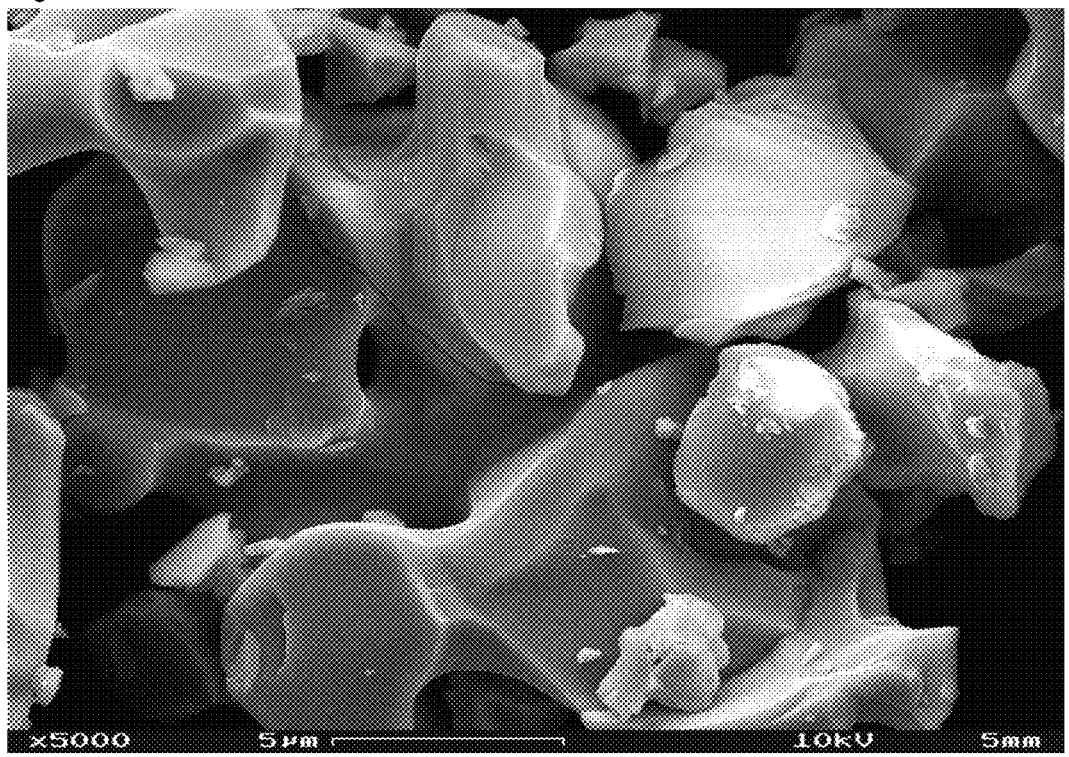

A composite powder of β-tricalcium phosphate particles and a polylactide (PDLLA) was prepared in accordance with the method described in JP 62083029 A using the NHS-1 apparatus. It was cooled with water at 12° C. A polylactide granulate 3 was used as mother particles and β-tricalcium phosphate (β-TCP; $d_{20}=30$ μm; $d_{50}141$ μm; $d_{90}=544$ μm) was used as baby particles. The SEM image of the β-TCP used is shown in FIG. 9a and FIG. 9b.

30.0 g of polylactide granulate were mixed with 20.0 g of β-TCP powder and were filled at 6,400 rpm. The rotor speed of the unit was set to 6,400 rpm (80 m/s) and the metered materials were processed for 10 min A total of 5 repetitions with equal material quantities and machine settings was carried out. A total amount of 249 g of composite powder was obtained. The product was sieved to remove the coarse fraction >250 μm where possible (manual dry-sieving through a 250 μm sieve). Then, the fine-grain fraction <20 μm was separated through a 20 μm sieve by means of an air jet sieving machine.

EXAMPLE 9

A composite powder of rhombohedral calcium carbonate particles and a polylactide (PDLLA) was prepared in accordance with the method described in JP 62083029 A using the NHS-1 apparatus. It was cooled with water at 12° C. A polylactide granulate 3 was used as mother particles and rhombohedral calcium carbonate particles ($d_{20}=11$ μm; $d_{50}=16$ μm; $d_{90}=32$ μm) were used as baby particles.

30.0 g of polylactide granulate were mixed with 20.0 g of the rhombohedral calcium carbonate particles and were filled at 6,400 rpm. The rotor speed of the unit was set to 6,400 rpm (80 m/s) and the metered materials were processed for 10 min. A total of 5 repetitions with equal material quantities and machine settings was carried out. A total amount of 232 g of composite powder was obtained. The product was sieved to remove the coarse fraction >250 μm where possible (manual dry-sieving through a 250 μm sieve). Then the fine-grain fraction <20 μm was separated through a 20 μm sieve by means of an air jet sieving machine.

EXAMPLE 10

A composite powder of ground calcium carbonate particles and a polylactide (PDLLA) was prepared in accordance with the method described in JP 62083029 A using the NHS-1 apparatus. It was cooled with water at 12° C. A polylactide granulate 3 was used as mother particles and ground calcium carbonate (GCC; $d_{20}=15$ μm; $d_{50}=46$ μm; $d_{90}=146$ μm) were used as baby particles.

30.0 g of polylactide granulate were mixed with 20.0 g of GCC and were filled at 6,400 rpm. The rotor speed of the unit was set to 6,400 rpm (80 m/s) and the metered materials were processed for 10 min A total of 5 repetitions with equal material quantities and machine settings was carried out. A total amount of 247 g of composite powder was obtained. The product was sieved to remove the coarse fraction >250 μm where possible (manual dry-sieving through a 250 μm sieve). Then, the fine-grain fraction <20 μm was separated through a 20 μm sieve by means of an air jet sieving machine.

TABLE 3

| | Example 3 | Example 4 | Example 5 | Example 6 | Example 7 | Comparison 1 |
|---|---|---|---|---|---|---|
| Composition for the preparation of the composite powder with microstructured particles | | | | | | |
| m(Example 1) [Gew.-%] | 40 | 40 | 0 | 40 | 40 | 20 |
| m(Example 2) [Gew.-%] | 0 | 0 | 40 | 0 | 0 | 0 |
| Polylactide | Granulate 1 | Granulate 1 | Granulate 1 | Granulate 2 | Granulate 3 | Granulate 3 |
| m(Polylactide) [Gew.-%] | 60 | 60 | 60 | 60 | 60 | 80 |
| Preparation of the composite powder with microstructured particles | | | | | | |
| Sieving | <250 μm | <250 μm <20 μm (air separation) | <250 μm | <250 μm <20 μm (air jet sieving) | <250 μm <20 μm (air jet sieving) | <800 μm (for measurement of the particle size distribution) |
| $CaCO_3$ content [Gew.-%][1] | 41.0 | 22.4 | 35.0 | 19.5 | 22.3 | 22.4 (Mean value from 5 measurements) |
| $T_P$ [° C.][1] | 291 | 310 | 341 | 304 | 286 | 319 (Mean value from 5 measurements) |
| $d_{50}$ [μm][1] | 25 | 47 | 26 | 112 | 136 | 228 |
| Share <20 μm [Vol.-%][1] | 43.6 | 13.7 | 37.7 | 0.3 | 2.3 | 20.6 |
| $d_{20}$ [μm][1] | 9 | 26 | 14 | 69 | 80 | |
| $d_{90}$ [μm][1] | 86 | 102 | 70 | 223 | 247 | |
| $d_{20}/d_{50}$ [%] | 36 | 52 | 54 | 62 | 59 | |
| Moisture [Gew.-%][1] | 0.8 | 0.6 | 0.5 | 0.9 | 0.9 | 0.3 |
| Inherent viscosity [dl/g] | 1.0 | 1.0 | 0.9 | 1.9 | 1.9 | 1.9 |
| Three-point flexural strength [MPa] | 66 | 68 | 77 | 84 | 67 | 79 |

TABLE 3-continued

| | | | | | | |
|---|---|---|---|---|---|---|
| E modulus [N/mm$^2$] | 4782 | 3901 | 4518 | 3530 | 3594 | 3420 |
| flowability | 4 | 1 | 4 | 2 | 3 | 5 |
| Cytotoxicity test | non-cytotoxic | non-cytotoxic | non-cytotoxic | — | non-cytotoxic | non-cytotoxic |

| | Example 8 | Example 9 | Example 10 |
|---|---|---|---|
| Composition for the preparation of the composite powder with microstructured particles | | | |
| m(Filler) [Gew.-%] | 40 | 40 | 40 |
| Polylactide | Granulate 3 | Granulate 3 | Granulate 3 |
| m(Polylactide) [Gew.-%] | 60 | 60 | 60 |
| Preparation of the composite powder with microstructured particles | | | |
| Sieving | <250 μm <20 μm Air jet sieving | <250 μm <20 μm Air jet sieving | <250 μm <20 μm Air jet sieving |
| Filler content [Gew.-%]* | 24.9 | 24.2 | 26.6 |
| $T_P$ [° C.] | 341° C. | 303° C. | 303° C. |
| $d_{20}$ [μm] | 85 | 74 | 75 |
| $d_{50}$ [μm] | 131 | 128 | 120 |
| $d_{90}$ [μm] | 226 | 257 | 230 |
| Share <20 μm [Vol.-%] | 3.0 | 4.5 | 1.6 |
| Moisture [Gew.-%] | 0.6 | 0.6 | 0.6 |
| Inherent viscosity [dl/g] | 1.8 | 1.8 | 1.9 |

$^1$At least double determination

The invention claimed is:

1. A method for producing an implant using a composite powder having microstructured particles, the method comprising:
    bonding large particles to small particles,
    wherein the large particles comprise at least one polymer and have an average particle diameter in the range from 0.1 μm to 10 mm,
    wherein the small particles:
        are arranged on the surface of the large particles or are distributed non-homogeneously within the large particles, and
        comprise spherical precipitated calcium carbonate particles having an average diameter in the range from 0.05 μm to 50.0 μm,
    wherein the spherical precipitated calcium carbonate particles are obtained by:
        providing a calcium hydroxide suspension,
        introducing carbon dioxide or a gas mixture containing carbon dioxide into the calcium hydroxide suspension,
        separating the spherical precipitated calcium carbonate particles formed, and
        adding 0.3% by weight to 0.7% by weight of at least one aminotrialkylene phosphonic acid; and
    forming the implant by selective laser sintering of a composition comprising the composite powder,
    wherein the microstructured particles of the composite powder have an average particle size of $d_{50}$ within the range from 10 μm to less than 200 μm.

2. The method according to claim 1, further comprising adding at least one of: aminotrimethylene phosphonic acid, aminotriethylene phosphonic acid, aminotripropylene phosphonic acid or aminotributylene phosphonic acid obtain the spherical precipitated calcium carbonate particles.

3. The method according to claim 1, wherein introducing the carbon dioxide or the gas mixture containing carbon dioxide is performed until the reaction mixture has a pH value of less than 9.

4. The method according to claim 1, wherein the reaction of the calcium hydroxide suspension with the carbon dioxide or the gas mixture containing carbon dioxide is carried out at a temperature of less than 25° C.

5. The method according to claim 1, wherein at least one of:
    the carbon dioxide or the gas mixture containing carbon dioxide is introduced into the calcium hydroxide suspension with a gas flow rate in the range from 0.02 l $CO_2$/(h*g $Ca(OH)_2$) to 2.0 l $CO_2$/(h*g $Ca(OH)_2$),
    the spherical calcium carbonate particles have a mean diameter greater than 3.0 μm,
    the spherical calcium carbonate particles have an average diameter of less than 30.0 μm,
    the spherical calcium carbonate particles have a size distribution in which at least 90.0% by weight of all calcium carbonate particles have a particle diameter in the range from mean particle diameter −30% to mean particle diameter+30%, or
    the spherical calcium carbonate particles have a form factor of greater than 0.90, defined as the quotient of minimum particle diameter and maximum particle diameter.

6. The method according to claim 1, wherein the large particles comprise at least one thermoplastic polymer.

7. The method according to claim 1, wherein the large particles comprise at least one resorbable polymer.

8. The method according to claim 7, wherein the resorbable polymer has an inherent viscosity, measured in chloroform at 25° C. with 0.1% polymer concentration, in the range from 0.3 dl/g to 8.0 dl/g.

9. The method according to claim 1, wherein at least one of:
    the large particles comprise poly-D-, poly-L- or poly-D, L-lactic acid,
    the large particles comprise at least one resorbable polyester having a number average molecular weight in the range from 500 g/mol to 1,000,000 g/mol,
    the large particles comprise at least one polyimide,
    the large particles comprise at least one polyurethane,
    the proportion by weight of the spherical precipitated calcium carbonate particles, based on the total weight of the composite powder, is at least 0.1% by weight, or the composite powder, based on the total weight of the composite powder, comprises 40.0 wt. % to 80.0 wt. % PLLA and 20.0 wt. % to 60.0 wt. % of the spherical precipitated calcium carbonate particles.

10. A method for forming an implant having spherical calcium carbonate particles, the method comprising:
providing a calcium hydroxide suspension;
introducing carbon dioxide or a gas mixture containing carbon dioxide into the calcium hydroxide suspension;
separating the spherical calcium carbonate particles formed;
adding 0.3% by weight to 0.7% by weight of at least one aminotrialkylene phosphonic acid; and
forming the implant by selective laser sintering of a composition comprising the spherical calcium carbonate particles,
wherein the spherical calcium carbonate particles of the composition have an average particle size $d_{50}$ within the range from 10 μm to less than 200 μm.

11. The method according to claim 10, wherein the spherical calcium carbonate particles are used as an additive for the implant which implant is prepared for in medical technology.

12. The method according to claim 2, wherein introducing the carbon dioxide or the gas mixture containing carbon dioxide is performed until the reaction mixture has a pH value of less than 9.

13. The method according to claim 2, wherein the reaction of the calcium hydroxide suspension with the carbon dioxide or the gas mixture containing carbon dioxide is carried out at a temperature of less than 25° C.

14. The method according to claim 3, wherein the reaction of the calcium hydroxide suspension with the carbon dioxide or the gas mixture containing carbon dioxide is carried out at a temperature of less than 25° C.

15. The method according to claim 2, wherein at least one of:
the carbon dioxide or the gas mixture containing carbon dioxide is introduced into the calcium hydroxide suspension with a gas flow rate in the range from 0.02 l $CO_2$/(h*g Ca(OH)$_2$) to 2.0 l $CO_2$/(h*g Ca(OH)$_2$),
the spherical calcium carbonate particles have a mean diameter greater than 3.0 μm,
the spherical calcium carbonate particles have an average diameter of less than 30.0 μm,
the spherical calcium carbonate particles have a size distribution in which at least 90.0% by weight of all calcium carbonate particles have a particle diameter in the range from mean particle diameter −30% to mean particle diameter+30%, or
the spherical calcium carbonate particles have a form factor of greater than 0.90, defined as the quotient of minimum particle diameter and maximum particle diameter.

16. The method according to claim 3, wherein at least one of:
the carbon dioxide or the gas mixture containing carbon dioxide is introduced into the calcium hydroxide suspension with a gas flow rate in the range from 0.02 l $CO_2$/(h*g Ca(OH)$_2$) to 2.0 l $CO_2$/(h*g Ca(OH)$_2$),
the spherical calcium carbonate particles have a mean diameter greater than 3.0 μm,
the spherical calcium carbonate particles have an average diameter of less than 30.0 μm,
the spherical calcium carbonate particles have a size distribution in which at least 90.0% by weight of all calcium carbonate particles have a particle diameter in the range from mean particle diameter −30% to mean particle diameter+30%, or
the spherical calcium carbonate particles have a form factor of greater than 0.90, defined as the quotient of minimum particle diameter and maximum particle diameter.

17. The method according to claim 4, wherein at least one of:
the carbon dioxide or the gas mixture containing carbon dioxide is introduced into the calcium hydroxide suspension with a gas flow rate in the range from 0.02 l $CO_2$/(h*g Ca(OH)$_2$) to 2.0 l $CO_2$/(h*g Ca(OH)$_2$),
the spherical calcium carbonate particles have a mean diameter greater than 3.0 μm,
the spherical calcium carbonate particles have an average diameter of less than 30.0 μm, in particular less than 20.0 μm,
the spherical calcium carbonate particles have a size distribution in which at least 90.0% by weight of all calcium carbonate particles have a particle diameter in the range from mean particle diameter −30% to mean particle diameter+30%, or
the spherical calcium carbonate particles have a form factor of greater than 0.90, defined as the quotient of minimum particle diameter and maximum particle diameter.

18. The method according to claim 2, wherein the large particles comprise at least one thermoplastic polymer.

19. The method according to claim 3, wherein the large particles comprise at least one thermoplastic polymer.

20. A method for producing an implant using a composite powder having microstructured particles, the method comprising:
bonding large particles to small particles,
wherein the small particles:
are arranged on the surface of the large particles or are distributed non-homogeneously within the large particles, and
comprise spherical precipitated calcium carbonate particles having an average diameter in the range from 0.05 μm to 50.0 μm;
wherein the spherical precipitated calcium carbonate particles are obtained by:
providing a calcium hydroxide suspension,
introducing carbon dioxide or a gas mixture containing carbon dioxide into the calcium hydroxide suspension,
separating the spherical precipitated calcium carbonate particles formed, and
adding 0.3% by weight to 0.7% by weight of at least one aminotrialkylene phosphonic acid; and
forming the implant by selective laser sintering of a composition comprising the composite powder,
wherein the microstructured particles of the composite powder have an average particle size $d_{50}$ within the range from 10 μm to less than 200 μm.

* * * * *